(12) United States Patent
Bishop et al.

(10) Patent No.: US 9,440,054 B2
(45) Date of Patent: Sep. 13, 2016

(54) EXPANDABLE TRANSAPICAL SHEATH AND METHOD OF USE

(75) Inventors: Joseph Bishop, Menifee, CA (US); Jay Lenker, Laguna Beach, CA (US); Edward J. Nance, Corona, CA (US)

(73) Assignee: Onset Medical Corporation, Irvine, CA (US)

( * ) Notice: Subject to any disclaimer, the term of this patent is extended or adjusted under 35 U.S.C. 154(b) by 1298 days.

(21) Appl. No.: 12/258,245

(22) Filed: Oct. 24, 2008

(65) Prior Publication Data
US 2009/0287183 A1 Nov. 19, 2009

Related U.S. Application Data

(60) Provisional application No. 61/127,619, filed on May 14, 2008.

(51) Int. Cl.
*A61F 2/24* (2006.01)
*A61M 29/02* (2006.01)
(Continued)

(52) U.S. Cl.
CPC ............ *A61M 29/02* (2013.01); *A61F 2/2427* (2013.01); *A61M 25/0662* (2013.01); *A61M 25/104* (2013.01); *A61M 25/005* (2013.01); *A61M 2025/0024* (2013.01); *A61M 2025/0681* (2013.01)

(58) Field of Classification Search
CPC ......... A61M 25/0662; A61M 25/104; A61M 2025/0681
USPC .......................... 623/2.1–2.37, 2.11; 606/108
See application file for complete search history.

(56) References Cited

U.S. PATENT DOCUMENTS

| 4,338,942 A | 7/1982 | Fogarty |
|---|---|---|
| 4,401,433 A | 8/1983 | Luther |

(Continued)

FOREIGN PATENT DOCUMENTS

| EP | 0206553 | 1/1991 |
|---|---|---|
| WO | WO/99/17665 | 4/1999 |

(Continued)

OTHER PUBLICATIONS

International Search Report for PCT Application No. PCT/US2009/044030 the PCT counterpart of the present application, dated Dec. 28, 2009.

*Primary Examiner* — Gregory Anderson
*Assistant Examiner* — Christina Lauer
(74) *Attorney, Agent, or Firm* — Inskeep IP Group, Inc.

(57) ABSTRACT

Disclosed is an expandable transluminal sheath, for introduction into the body while in a first, small cross-sectional area configuration, and subsequent expansion of at least a part of the distal end of the sheath to a second, enlarged cross-sectional configuration. The sheath is configured for use in the vascular system and has utility in the introduction and removal of implant delivery catheters. The access route is through the ventricular myocardium, more specifically at the left ventricular apex, into the aortic root. The distal end of the sheath is maintained in the first, low cross-sectional configuration during advancement to the arteries into the aorta. The distal end of the sheath is subsequently expanded using a radial dilatation device, which is removed prior to the introduction of implant delivery catheters. In an exemplary application, the sheath includes a supported proximal end, a supported distal end, and a collapsible center section. Certain configurations of the sheath are capable of being inserted in a first, small cross-sectional configuration, being expanded diametrically to a second, larger cross-sectional configuration, and then being reduced to a diametrically small size for removal.

12 Claims, 20 Drawing Sheets

(51) Int. Cl.
*A61M 25/06* (2006.01)
*A61M 25/10* (2013.01)
*A61M 25/00* (2006.01)

(56) References Cited

U.S. PATENT DOCUMENTS

| | | | |
|---|---|---|---|
| 4,738,666 A | 4/1988 | Fuqua | |
| 5,053,007 A | 10/1991 | Euteneuer | |
| 5,059,183 A | 10/1991 | Semrad | |
| 5,092,839 A | 3/1992 | Kipperman | |
| 5,201,756 A | 4/1993 | Horzewski | |
| 5,201,901 A | 4/1993 | Harada et al. | |
| 5,250,025 A | 10/1993 | Soanowski et al. | |
| 5,263,964 A | 11/1993 | Purdy | |
| 5,295,994 A | 3/1994 | Bonutti | |
| 5,320,611 A | 6/1994 | Bonutti | |
| 5,358,495 A | 10/1994 | Lynn | |
| 5,391,172 A | 2/1995 | Williams | |
| 5,395,349 A | 3/1995 | Quiachon et al. | |
| 5,514,091 A | 5/1996 | Yoon | |
| 5,527,336 A | 6/1996 | Rosenbluth | |
| 5,630,801 A * | 5/1997 | Roussigne et al. | 623/1.11 |
| 5,662,614 A | 9/1997 | Edoga | |
| 5,669,936 A | 9/1997 | Lazarus | |
| 5,766,203 A | 6/1998 | Imran et al. | |
| 5,772,631 A | 6/1998 | Lepor | |
| 5,776,141 A | 7/1998 | Klein et al. | |
| 5,807,311 A | 9/1998 | Palestrant | |
| 5,824,002 A | 10/1998 | Gentelia et al. | |
| 6,125,852 A | 10/2000 | Stevens et al. | |
| 6,156,053 A | 12/2000 | Gandhi et al. | |
| 6,168,579 B1 | 1/2001 | Tsugita | |
| 6,183,443 B1 | 2/2001 | Kratoska et al. | |
| 6,197,016 B1 | 3/2001 | Fourkas et al. | |
| 6,264,633 B1 | 7/2001 | Knorig | |
| 6,299,628 B1 | 10/2001 | Harrison et al. | |
| 6,312,443 B1 | 11/2001 | Stone | |
| 6,358,238 B1 | 3/2002 | Sherry | |
| 6,537,247 B2 | 3/2003 | Shannon | |
| 6,616,678 B2 | 9/2003 | Nishtala et al. | |
| 6,638,268 B2 | 10/2003 | Niazi | |
| 6,679,871 B2 | 1/2004 | Hahnen | |
| 6,706,013 B1 | 3/2004 | Bhat et al. | |
| 6,706,017 B1 | 3/2004 | Dulguerov | |
| 6,802,319 B2 | 10/2004 | Stevens et al. | |
| 7,077,801 B2 | 7/2006 | Haverich | |
| 7,090,683 B2 | 8/2006 | Brock et al. | |
| 7,213,601 B2 | 5/2007 | Stevens et al. | |
| 7,320,704 B2 | 1/2008 | Lashinski et al. | |
| 7,341,584 B1 | 3/2008 | Starkey | |
| 7,361,137 B2 | 4/2008 | Taylor et al. | |
| 7,635,386 B1 * | 12/2009 | Gammie | 623/2.11 |
| 7,722,568 B2 * | 5/2010 | Lenker et al. | 604/164.03 |
| 7,780,692 B2 | 8/2010 | Nance et al. | |
| 7,892,203 B2 | 2/2011 | Lenker et al. | |
| 8,562,559 B2 | 10/2013 | Bishop et al. | |
| 2001/0003795 A1 | 6/2001 | Suresh et al. | |
| 2001/0012950 A1 | 8/2001 | Nishtala et al. | |
| 2002/0009535 A1 | 1/2002 | Michal et al. | |
| 2002/0077653 A1 | 6/2002 | Hudson et al. | |
| 2002/0099431 A1 | 7/2002 | Armstrong et al. | |
| 2003/0032974 A1 | 2/2003 | Leschinsky et al. | |
| 2003/0114913 A1 * | 6/2003 | Spenser et al. | 623/1.11 |
| 2003/0212384 A1 | 11/2003 | Hayden | |
| 2004/0006344 A1 | 1/2004 | Nguyen et al. | |
| 2005/0049667 A1 | 3/2005 | Arbefeuille et al. | |
| 2005/0085842 A1 | 4/2005 | Eversull et al. | |
| 2005/0119688 A1 | 6/2005 | Bergheim | |
| 2005/0124937 A1 | 6/2005 | Kick et al. | |
| 2005/0125021 A1 * | 6/2005 | Nance et al. | 606/192 |
| 2005/0149105 A1 | 7/2005 | Leeflang et al. | |
| 2005/0154442 A1 * | 7/2005 | Eidenschink et al. | 623/1.11 |
| 2005/0222576 A1 | 10/2005 | Kick et al. | |
| 2005/0240200 A1 | 10/2005 | Bergheim | |
| 2005/0251094 A1 | 11/2005 | Peterson | |
| 2005/0251187 A1 | 11/2005 | Beane et al. | |
| 2005/0251251 A1 | 11/2005 | Cribier | |
| 2006/0020327 A1 | 1/2006 | Lashinski et al. | |
| 2006/0020333 A1 | 1/2006 | Lashinski et al. | |
| 2006/0020334 A1 | 1/2006 | Lashinski et al. | |
| 2006/0025854 A1 | 2/2006 | Lashinski et al. | |
| 2006/0025855 A1 | 2/2006 | Lashinski et al. | |
| 2006/0025857 A1 | 2/2006 | Bergheim et al. | |
| 2006/0027116 A1 | 2/2006 | Salzer | |
| 2006/0074397 A1 | 4/2006 | Shimada | |
| 2006/0074476 A1 | 4/2006 | Holman et al. | |
| 2006/0074484 A1 * | 4/2006 | Huber | 623/2.11 |
| 2006/0135962 A1 * | 6/2006 | Kick et al. | 606/108 |
| 2006/0135981 A1 | 6/2006 | Lenker et al. | |
| 2006/0142848 A1 | 6/2006 | Gabbay | |
| 2006/0161193 A1 | 7/2006 | Beane et al. | |
| 2006/0167468 A1 | 7/2006 | Gabbay | |
| 2006/0178675 A1 | 8/2006 | Hamman | |
| 2006/0241544 A1 | 10/2006 | Haverich | |
| 2006/0259137 A1 | 11/2006 | Artof et al. | |
| 2007/0027534 A1 | 2/2007 | Bergheim et al. | |
| 2007/0060880 A1 | 3/2007 | Gregorich et al. | |
| 2007/0078510 A1 | 4/2007 | Ryan | |
| 2007/0213813 A1 | 9/2007 | Von Segesser et al. | |
| 2007/0254273 A1 | 11/2007 | LaFrance et al. | |
| 2007/0265643 A1 | 11/2007 | Beane et al. | |
| 2007/0269784 A1 | 11/2007 | LaFrance et al. | |
| 2007/0270944 A1 | 11/2007 | Bergheim et al. | |
| 2007/0282429 A1 | 12/2007 | Hauser et al. | |
| 2008/0015687 A1 | 1/2008 | Lashinski et al. | |
| 2008/0021546 A1 | 1/2008 | Patz et al. | |
| 2008/0029105 A1 | 2/2008 | Stevens et al. | |
| 2008/0071361 A1 | 3/2008 | Tuval et al. | |
| 2008/0071362 A1 | 3/2008 | Tuval et al. | |
| 2008/0071363 A1 | 3/2008 | Tuval et al. | |
| 2008/0071366 A1 | 3/2008 | Tuval et al. | |
| 2008/0071368 A1 | 3/2008 | Tuval et al. | |
| 2008/0071369 A1 | 3/2008 | Tuval et al. | |
| 2008/0082079 A1 | 4/2008 | Braga et al. | |
| 2008/0082164 A1 | 4/2008 | Friedman | |
| 2008/0097595 A1 | 4/2008 | Gabbay | |
| 2008/0109065 A1 | 5/2008 | Bowe | |
| 2008/0109073 A1 | 5/2008 | Lashinski et al. | |
| 2008/0140189 A1 | 6/2008 | Nguyen et al. | |
| 2008/0147160 A1 | 6/2008 | Ghione et al. | |
| 2008/0147180 A1 | 6/2008 | Ghione et al. | |
| 2008/0147181 A1 | 6/2008 | Ghione et al. | |
| 2008/0147182 A1 | 6/2008 | Righini et al. | |
| 2008/0161638 A1 | 7/2008 | Taylor et al. | |
| 2008/0177142 A1 | 7/2008 | Roskopf | |
| 2008/0177381 A1 | 7/2008 | Navia et al. | |
| 2008/0183136 A1 | 7/2008 | Lenker et al. | |
| 2008/0183273 A1 | 7/2008 | Mesana et al. | |
| 2008/0195199 A1 | 8/2008 | Kheradvar et al. | |
| 2008/0200980 A1 | 8/2008 | Robin et al. | |
| 2008/0208327 A1 | 8/2008 | Rowe | |
| 2008/0208329 A1 | 8/2008 | Bishop et al. | |
| 2008/0215144 A1 | 9/2008 | Ryan et al. | |
| 2008/0221439 A1 | 9/2008 | Iddan et al. | |
| 2008/0221440 A1 | 9/2008 | Iddan et al. | |
| 2008/0221442 A1 | 9/2008 | Tolkowsky et al. | |
| 2008/0234813 A1 | 9/2008 | Heuser | |
| 2009/0287182 A1 | 11/2009 | Bishop et al. | |
| 2010/0228077 A1 | 9/2010 | Lenker et al. | |
| 2011/0144690 A1 | 6/2011 | Bishop et al. | |
| 2011/0152763 A1 | 6/2011 | Bishop et al. | |

FOREIGN PATENT DOCUMENTS

| | | |
|---|---|---|
| WO | WO/03/090834 | 11/2003 |
| WO | WO 2006/029370 A2 | 3/2006 |
| WO | WO 2009/140546 A2 | 11/2009 |
| WO | WO 2011/032038 A2 | 3/2011 |

* cited by examiner

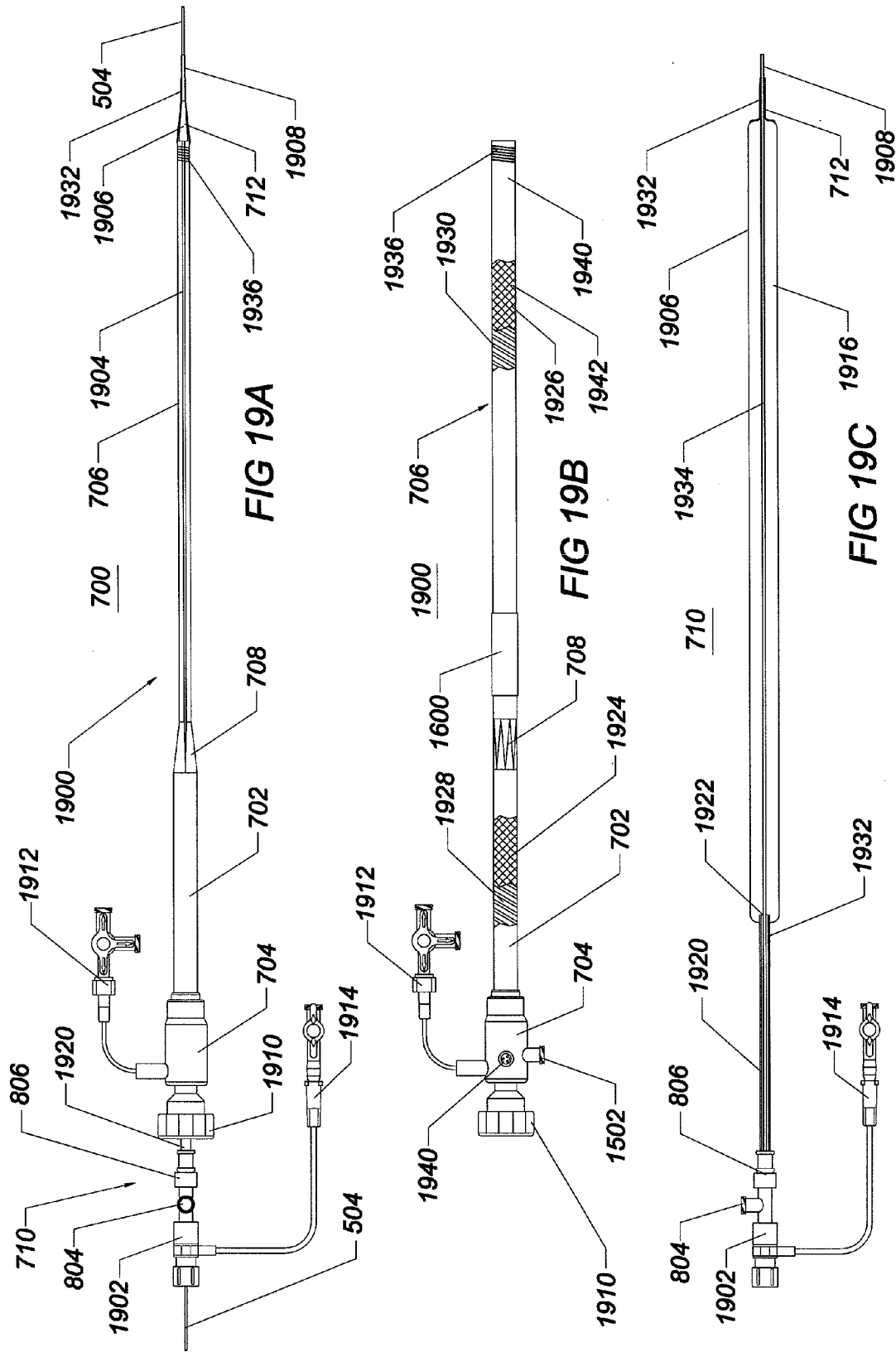

EXPANDABLE TRANSAPICAL SHEATH AND METHOD OF USE

PRIORITY CLAIM

This application claims priority to U.S. Provisional Patent Application Ser. No. 61/127,619, filed May 14, 2008, titled Expandable Iliac Sheath and Method of Use, and U.S. patent application Ser. No. 12/021,097, filed Jan. 28, 2008, titled Expandable Intra Aortic Balloon Pump Sheath, the entirety of which are hereby incorporated herein by reference.

BACKGROUND OF THE INVENTION

1. Field of the Invention

The invention relates to medical methods and devices and, more particularly, to methods and devices for accessing the chambers of the heart through a myocardial puncture.

2. Description of the Related Art

Considerable effort and money is being directed toward replacement of diseased or damaged cardiac valves through minimally invasive techniques. Current approaches for aortic valve replacement include trans-catheter access from an iliac or femoral artery catheter insertion point. Another procedure being explored is transapical valve replacement. The procedure for transapical aortic valve replacement involves surgically accessing the heart through the fourth or fifth intercostal space, dividing the pericardium to expose the heart, making an incision in the heart, dilating the incision, and performing the valve replacement procedure through the dilated incision in the apex of the ventricular myocardium, while the heart continues to beat and function.

Transapical aortic valve implantation (TA-AVI) is being evaluated in patients suffering symptomatic aortic stenosis and an increase perioperative risk. Transapical access is based on clinical experience with de-airing the heart, through the tip (apex) of the left ventricle, during routine cardiac surgical interventions. Insertion of a catheter, and follow-on closure, through the apex is possible in a relatively uncomplicated manner. An anterolateral mini-thoracotomy provides a relatively simple and standardized access to the apex of the heart. This procedure is applicable in almost all patients and they can be extubated soon afterwards. The mini-thoracotomy procedure can be performed without intubation under regional anesthesia in some patients.

From the apex of the left ventricle, the aortic valve can be readily accessed. The major advantage of transapical access is a direct, and antegrade, approach to the aortic valve. By virtue of short distances and direct access, precise positioning of an aortic valve prosthesis inside the stenosed native valve can be executed from the left ventricular apex. An additional benefit of the technique is minimal manipulation in the aortic arch. This is definitively associated with reduced risk of mobilizing intravascular calcifications and thus with a reduced stroke risk. The lower stroke risk of the transapical, in comparison to the trans-femoral, aortic valve implantation technique, has been published in the medical literature.

Transapical aortic valve replacement procedures are performed by a team comprising cardiac surgeons, cardiologists, and anesthetists. High quality imaging, including fluoroscopy, is required and the procedures are performed in the setting of a hybrid operative theatre suitable for both catheterization and open heart cardiothoracic surgery.

TA-AVI can be performed as an off-pump procedure. Femoral guidewires are placed to be able to convert to cardiopulmonary bypass for the safety of the patient in case a bail-out is required. The apex is reached by means of an anterolateral mini-thoracotomy in the fourth, fifth, or sixth intercostal space. Purse string sutures are placed at the apex. Valve implantation is then performed over guidewires that are antegradely inserted under fluoroscopic visualization. The apex can be closed using the prepositioned purse string sutures after completion of the procedure. The chest is then closed in a routine fashion. The patient can then be extubated and moved to the recovery area.

Suggested further reading related to transapical valve replacement includes: Beyersdorf, F, Transapical Transcatheter Aortic Valve Implantation, *Eur J Cardiothoracic Surg*, 2007; 31:7-8, and Jian Ye, et al. Six-Month Outcome of Transapical Transcatheter Arotic Valve Implantation in the Intial Seven Humans, *European J Cardio Thorac Surg*, 2007; 31:16-21, the entirety of which are incorporated by reference herein Current access systems are relatively crude and suboptimal for transapical procedures. It would be desirable to have an improved sheath that would maximize access while minimizing myocardial trauma, procedure time, comorbidities, as well as improving healing and patient outcomes.

SUMMARY OF THE INVENTION

One arrangement comprises an transapical introducer sheath that includes an axially elongate structure having a proximal end, a distal end, and a lumen extending therethrough, is disclosed. The transapical introducer sheath comprises at least a portion of its length being expandable, wherein the expandable region has a first, smaller cross-sectional area and a second, larger cross-sectional area. The expandable transapical introducer sheath can comprise a hub and a length of sheath tubing. In certain embodiments, the sheath tubing has a proximal section and a distal section. The proximal section can be partially expandable, fully expandable, or completely non-expandable in a direction lateral to that of the longitudinal axis of the axially elongate introducer sheath. Such expansion can be termed diametric, radial, or lateral. In an embodiment, the distal section can be expandable. The introducer sheath is suitable for access to the interior of the heart through the myocardium. In exemplary embodiments, the expandable transapical introducer sheath is configured to provide access to the left ventricle through the left ventricular apex.

In one embodiment, the sheath can be used as an introducer for therapeutic or diagnostic catheter systems or devices. The expandable sheath has the clinical benefit of being able to radially dilate tissue, thus causing minimal tearing and tissue trauma relative to surgical incisions that generally tear tissue in order to expand. The expandable sheath can be used to assist with percutaneous, port-access, or minimally invasive cardiac access procedures in that it allows for a small diameter access to the cardiac chambers that can then be expanded into a size large enough for introduction of large interventional, therapeutic, or diagnostic devices therethrough. The expandable arterial access sheath can reduce procedure time, procedure cost, trauma to the patient, and improve patient outcomes.

Other embodiments include the procedures or methods for treating the heart or central cardiovascular system. The methods, or procedures can be performed, in certain embodiments, as follows:

The pericardium, overlaying the left ventricular apex of the heart is exposed by making a 4-5 cm incision through the patient's fourth, fifth, or sixth intercostal space. The pericardium is next opened and retracted to provide a stable, adequate left ventricular apical exposure. Two opposing, plegeted purse string sutures are placed in the apical myocardium, with a circumference of sufficient diameter to accommodate the full diameter of an introducer. Provision is made to ensure an adequate tissue barrier between the introducer and suture to prevent the suture from pulling through with tension and/or device insertion, especially during wound closure at the end of the procedure. An epicardial pacing wire is placed on the left ventricle. An 18-gauge needle is inserted, under fluoroscopic control. The needle can range between 16 and 22 gauge depending on the guidewire selected by the operator for initial insertion, annuloplasty catheter/balloon and/or deployment device. Under fluoroscopic control, the guidewire is directed through the access needle, intra-ventricular space, native aortic valve and well over the aortic arch, taking care to avoid those structures associated with the mitral valve. A balloon expandable sheath with a folded, or compressed, delivery size of about 14 to 18 French, or less, depending on the expanded size, is gently advanced over the guidewire, through the myocardium, to an appropriate position below the native aortic valve annulus. The dilating balloon can be inflated to a pressure and diameter to adequately deploy an approximately 18 to 30 French or larger ID expandable sheath. Once fully expanded, the balloon can be deflated to a negative pressure and removed through the proximal Tuohy-Borst or other hemostasis valve. The dilator system is now fully removed from the patient's heart. Hemostasis will be established with the hemostasis valve that is capable of sealing even when no dilator or other catheter is inserted therethrough. An approximately 20 French (or larger) inflated size valvuloplasty balloon, or other appropriate size, can be inserted, in its diametrically collapsed state, into the diseased aortic root. The balloon can then be inflated, under fluid pressure, to develop the largest native annulus possible to accept the prosthetic valve. The balloon can be deflated and the result assessed and repeated, if necessary, following which the valvuloplasty balloon can be removed.

Present systems may require pacing the heart at rates of 150 to 170 beats per minute. This may present an unsafe condition in the older, diseased heart. This pacing can be performed at a rate that will diminish cardiac output and thus relieve pressure on the ventricle and allow balloon inflation which will block the flow of blood between the left ventricle and the aorta. There is a limit on the duration of this procedure. Once the diseased annulus is sufficiently prepared to accept the prosthetic valve, the valvuloplasty balloon is removed and set aside. The prosthetic valve, premounted to a delivery catheter is inserted to the desired position in the aortic root. Rapid pacing can be initiated to diminish cardiac output. A valve delivery catheter dilator balloon can be expanded to deploy the prosthetic valve and embed the valve within the valve annulus. In other embodiments, the prosthetic valve can comprise a self-expanding fixation stent to anchor the valve within the natural valve annulus. The self-expanding fixation stent, such as one comprising nitinol or other spring element biased in a fully expanded configuration, can anchor the prosthetic valve in the natural valve annulus without the need of a separate dilator, dilator balloon, or the like.

In some embodiments, the distal section can comprise a polymeric wall with reinforcing elements that provide a degree of retention of cross-sectional shape. The distal section can comprise weak reinforcing elements that provide some control over the shape of the polymeric wall but are easily deformed into a collapsed configuration upon exposure to external forces such as those imposed by a blood vessel wall. In other embodiments, the sheath can comprise shape memory reinforcing elements fabricated from nitinol, for example. The distal section can be malleably expanded while in its Martensitic phase and then heated to a temperature above body temperature to cause a shape memory phase shift into a smaller, collapsed diameter suitable for removal from the patient.

In other embodiments, the distal end of the sheath can comprise a flared component that becomes larger in diameter moving distally. The flared component can comprise a taper or a reverse taper, or it can comprise a taper and a region of relatively constant diameter affixed or integral to the tapered region at its most distal end. The flared component can be integral to the distal end of the expandable portion of the sheath, or it can be affixed thereto. The flared component can be expanded using a balloon dilator, it can be expanded using self-expansion modalities, or it can comprise self-expansion with balloon dilator assist. The self-expansion can be due to resilient spring forces, or due to shape memory forces generated by sheath reinforcement components fabricated from nitinol, or other shape memory materials. The flared configuration can facilitate re-capture or removal of instruments or implantable devices such as percutaneously delivered aortic heart valves. In an exemplary embodiment, the flared configuration can also facilitate removal of the natural aortic valve root, should excision of the aortic valve root be required. The expandable, flared region of the sheath can range in length between 1-cm and 10-cm, with a preferred range of 2-cm to 5-cm. In an embodiment, the flared region can use the same balloon as the rest of the distal expandable region for expansion, or it can be expanded by a separate balloon.

In some embodiments, the proximal end of the sheath can comprise a hub incorporating one or more hemostasis-type valves. The hub can comprise a single catheter insertion port or it can comprise a plurality of catheter insertion ports. Each catheter insertion port preferably comprises hemostasis valves, stopcocks, or the like to prevent blood leakage from the catheter. The hub can further comprise one or more purge ports, which operably connect to the internal lumen of the hub and are terminated by stopcocks or other valves.

In some embodiments, the diametrically or radially expandable elements of the catheter can be configured as a tube having a plurality of longitudinal folds. The expandable regions or elements, located in the proximal section, distal section, or the center section of the sheath or catheter, can be creased into these folds and bent to form a first, smaller, folded cross sectional area. The expandable regions or elements can be folded over a central dilator catheter comprising, for example, an angioplasty-type balloon, a catheter shaft, a balloon inflation port at the proximal end, a guidewire lumen, and the like. Upon selective inflation of the angioplasty-type, non-elastomeric, non-distensible, balloon by application of fluid pressure into an appropriate port on the proximal end of the dilator catheter, the expandable regions can unfold into a second, larger, cross-sectional shape. The central dilator catheter can be deflated and removed from the sheath to create a large cross-section, center lumen suitable for the introduction of catheters, delivery catheters, implantable devices, and the like.

In an exemplary embodiment, the expandable introducer sheath comprises a proximal, non-expandable section. The proximal section comprises a composite tubular structure fabricated from an inner polymeric layer of polyethylene, an outer polymeric layer of polyethylene, and a reinforcement layer sandwiched between the two polymer layers. The reinforcement layer can comprise a coil of flat, spring-hardness, stainless steel wire or ribbon with a width of about 0.010 inches, with a range of 0.005 to 0.025 inches, and a thickness of about 0.003 inches, with a range of 0.002 to 0.004 inches. The coil spacing can range between 0.001 inches and 0.050 inches. The proximal, non-expandable region is affixed at its proximal end to the sheath hub. The distal end of the proximal non-expandable region is affixed to the proximal end of a transition zone. The distal end of the transition zone can be affixed to a distal expandable region.

The distal expandable region can comprise between 10% and 95% of the catheter shaft length. The distal, expandable region can comprise a reinforcing layer of malleable stainless steel ribbon or flat wire wound into a coil with similar dimensions as in the proximal region. The entire length, or a substantial portion thereof, can comprise an additional reinforcing layer, or layers, of braided material fabricated from materials such as, but not limited to, polyethylene naphthalate (PEN), polyester (PET), stainless steel, titanium, nitinol, cobalt nickel alloy, polyamide, polyimide, or the like. In an embodiment, the reinforcing structure, generally sandwiched between an outer and an inner layer of polymeric wall, can comprise an inner layer of polymer overlaid by a first reinforcing braid layer, overlaid by a coil reinforcement, finally overlaid with an outside layer of polymeric material. In another embodiment, the inner layer of polymeric material is overlaid by the coil reinforcement, which is overlaid by the braided reinforcement, which is finally overlaid with the outside layer of polymeric material. In yet another embodiment, the inner layer of polymeric material is overlaid by the braided layer, which is overlaid by the coil winding, which is overlaid by another layer of braid, which is finally overlaid by the outer polymeric layer.

In an embodiment, the sheath dilator is configured with a PET balloon affixed to a Hytrel shaft. The Hytrel shaft can comprise an inner and an outer tube concentrically disposed with an annulus between the two tubes. The distal end of the dilator balloon can be affixed to the inner Hytrel tubing. The proximal end of the dilator balloon is larger in diameter and is affixed to the outer Hytrel tubing in this embodiment. The outer Hytrel tubing extends just inside the center volume of the dilator balloon and the annulus between the outer tube and the inner tube is in fluid communication, operably connected to, the center volume of the dilator balloon. The annulus is operably in fluid communication with an inflation port integral to, or affixed to, the dilator hub. In another embodiment, an outer polymer tube, such as the outer Hytrel tube of the preceding embodiment, can be omitted and the dilator balloon can comprise a proximal tail that extends proximally to bond and seal within the dilator hub or sidearm. In this embodiment, the pressurization annulus for the balloon resides between the dilator balloon and the inner polymer tube, the pressurization annulus being operably connected to an inflation port on the dilator hub. The interior of the inner dilator tube comprises a guidewire lumen, with a diameter of, for example 0.037 to 0.042 inches, suitable for advancing the entire system over a guidewire suitable for aortic access. Such aortic access guidewires typically are 0.035 or 0.038 inches in diameter and are relatively stiff.

The sheath can be folded into one or more longitudinally oriented folds and wrapped around the dilator, with collapsed dilator balloon. The malleable elements in the distal expandable regions maintain the configuration of the system in its collapsed state. An optional outer jacket, which can have attached, peel-away, tear-away, or removable before use configurations, can be used to encase part or all of the diametrically collapsed sheath tubing. In other embodiments, the sheath can further comprise a thin FEP, PFA, or polytetrafluoroethylene (PTFE) tube over the outside of the sheath. This fluoropolymer outer covering need not be removed, its function being to protect a soft polyethylene sheath material from hard vascular deposits such as atheroma.

In yet another embodiment, the central region can comprise elastomeric polymer structure with an optional braid reinforcement that permits the central region to simply expand diametrically from a first smaller diameter to a second larger diameter without the use of folds. An internal slip layer of PTFE, FEP, PFA, or other highly lubricious material can be used to facilitate passage of a catheter through the central region to prevent clinging. The internal slip layer can be the inner layer of the polymer sandwich within which the reinforcing coils or braids are embedded.

Once the expandable, transapical introducer sheath system has been advanced so that its distal end reaches proximate, or through the aortic valve annulus, the dilator is expanded at pressures of between 10 and 40 atmospheres, and preferably between 15 and 30 atmospheres. The dilator is next deflated and removed from the central lumen of the sheath subassembly.

In other embodiments, the sheath can comprise a flexible shaft configured with an elastomeric outer membrane and a reinforcing layer configured as a braided structure that is capable of changing its diameter. The sheath can be inserted into a patient in a first, smaller cross-sectional configuration, preferably over a small diameter dilator or tapered obturator. The obturator or tapered dilator is next removed and a hollow central dilator of large diameter is inserted into the interior lumen of the sheath. Upon insertion of the large diameter, hollow central dilator into the flexible shaft of the sheath, the sheath can expand diametrically to a second, larger, cross-sectional area, diameter, or radius. One or more catheters can be inserted therethrough to reach a target site within the vasculature. Following completion of the procedure, the central dilator can be removed resulting in elastomeric contraction of the outer membrane to a first, smaller cross-sectional area. The sheath can next be removed from the patient in its first, smaller, cross-sectional area configuration. The sheath can be configured using principles and design elements as described in U.S. Pat. No. 7,309,334 by Gerard von Hoffmann, titled "Intracranial Aspiration Catheter", the entirety of which is hereby incorporated herein by reference.

The reinforcement of the expandable regions can comprise wire, preferably malleable wire. The wire can have a round cross-section, a rectangular cross-section, a ribbon-like cross-section, or the like. The malleable wire can be bent by a dilator balloon, tapered dilator, hollow dilator, or the like, into the second, larger cross-section and the strength of the malleable wire can substantially overcome any resilient springback imparted by the polymeric component of the sheath wall.

In other embodiments, the wire can have elastomeric properties or shape memory properties. These embodiments can utilize shape-memory wire, pseudoelastic wire, super-elastic wire, elastomeric wire, or the like. The wire can be nitinol, stainless steel, cobalt nickel alloy, or the like. The wire, in its shape-memory configuration can have an austenite finish temperature of around 25 to 35 degrees centigrade, preferably between 28 and 32 degrees centigrade so that body temperature blood causes the wire mesh to be biased to its larger, expanded configuration.

In another embodiment, the expandable region can comprise polymeric encapsulation of a braided or otherwise expandable shape memory reinforcing structure. The reinforcing elements or structure can have shape-memory characteristics. The sheath is inserted into the patient in its first, small cross-sectional area. The reinforcing elements are maintained below the martensite start temperature so that the reinforcing elements are substantially malleable, even at body temperature (approximately 37° C.). The sheath wall is next dilated with the balloon dilator as described herein. The dilator is next removed and the sheath becomes host to therapeutic or diagnostic catheters, which are inserted therethrough. Following removal of the catheters, electricity can be applied to lead wires at the proximal end of the sheath. The electrical leads are operably connected to heaters in the vicinity of the reinforcing elements, or the electrical leads are operably connected to each end of the reinforcing elements. The electricity causes Ohmic or resistive heating of the reinforcing elements to above their austenite finish temperature. The reinforcing structure, having been shape-set in its small diameter configuration, returns to that small diameter configuration, bringing the entire expandable sheath wall down with it, to facilitate removal of the sheath from the patient. An austenite finish (Af) temperature of around 42° C., or higher, can be used in this application.

The dilator catheter tubing can comprise an inner and outer member. The materials of the inner member and the outer member can comprise Hytrel, Pebax, polyether ether ketone (PEEK), composite, reinforced construction, polyester, polyurethane, polyethylene, or the like. The catheter hub can be fabricated from materials such as, but not limited to, polycarbonate, acrylonitrile butadiene styrene (ABS), polyurethane, polyvinyl chloride, and the like. The dilator balloon can be fabricated from stretch blow-molded polyester polyamide, polyamide, or polyester blends, using materials such as, for example, Eastman PET 9921 or similar.

In another embodiment, a coating can be applied to the expandable areas to generate an inwardly biased, radially oriented contraction force on the sheath. The expandable area can be forced to expand radially against the bias force of the coating. Once the radial expansion force is removed, the expandable area remains biased radially inward toward its smallest diameter, to which it will travel unless prevented from doing so. An internal dilator can be advanced axially, in the distal direction, into the lumen defined within the expandable distal region of the sheath. The internal dilator can maintain the sheath open lumen until removed proximally, at which point the sheath distal expandable tubing can contract in diameter back to a smaller size. This reduction in sheath diameter can be beneficial if performed prior to sheath removal since it reduces shear force on the myocardium during sheath removal and can improve the healing response of the tissue.

The system can comprise radiopacity enhancements to improve visualization under fluoroscopy. Radiopaque (RO) markers can be affixed to the distal end of the sheath to denote its distal end, the extents of the expandable region or regions, or even the orientation of the sheath by mounting the RO markers asymmetrically on the tubing. The radiopaque markers can comprise bands or windings of metal such as, but not limited to, tantalum, platinum, platinum iridium, gold, and the like.

In certain embodiments of the sheath wall construction, an inner layer of polymer and an outer layer of polymer sandwich a reinforcing layer. The reinforcing layer can be a coil of metal such as, but not limited to, titanium, stainless steel, cobalt nickel alloy, nitinol, tantalum, and the like. In the distal, expandable region, the coil is preferably malleable, with little or no spring properties, and does not exhibit any elastomeric tendencies. The coil can be fabricated from flat wire with a thickness of about 0.001 to 0.010 inches and preferably about 0.002 to 0.005 inches. The width of the flat wire can range from about 0.005 to 0.050 inches and preferably from about 0.008 to 0.025 inches. The spacing between the coils can, for example range from substantially 0 to approximately 5 times the width of the coil wire. The coil spacing should be non-zero to permit bonding of the outer layer and the inner layer of polymer surround on the sheath, thus a coil spacing of about 0.5 to 3 times the coil width is preferred. The coils can be fabricated from round stock, flat stock, or the like. The reinforcement can be sandwiched between the inner layer and the outer layer of polymeric material, wherein the inner and outer layers can be bonded or welded to each other through the space between the coils. The inner and outer polymeric layers can be fabricated from the same or different materials. Suitable materials for the inner and outer layers include, but are not limited to, polyurethane, silicone, Hytrel, Pebax, PEEK, polyethylene (PE), high density polyethylene (HDPE), low density polyethylene (LDPE), polyester, polyethylene blends, and the like. In yet another embodiment, a plastically deformable, malleable, or annealed, braid structure can also be used for reinforcement to beneficially eliminate the need for the malleable coil and permit a reduction in wall thickness while retaining the tensile strength and torqueability of the braid.

In certain embodiments, the sheath shaft can comprise multiple regions of varying flexibility along the axial length of the shaft. In some embodiments, the catheter shaft can have at least two regions of different flexibility. In other embodiments, the catheter shaft can comprise three regions of different flexibility. In yet other embodiments, the sheath shaft flexibility can be reduced toward the proximal end of the catheter and increased moving toward the distal end of the catheter. Moving from the proximal to the distal end of the catheter shaft, the flexibility of a given discreet section can be greater than the flexibility of the region just proximal and adjacent to said discreet section. A sheath having a substantially collapsed, small diameter distal region can exhibit significantly increased flexibility in that area over its flexibility in non-expandable, or fully expanded, expandable regions. Following such traverse, the sheath can be expanded to create a stiffer, larger diameter structure.

Another aspect is the catheter apparatus configured to deliver a valve to the heart. In an embodiment, the delivery catheter for an aortic valve can be configured with a valve housing having an inner diameter ranging from about 14 French to about 32 French, with a preferred range of 18 French to 28 French. The length of the distal, expandable region of the sheath should equal at least the length of the left ventricle from the aortic root to the ventricular apex and can range between 15 cm and 40 cm.

Following completion of the procedure, the interventional catheters are removed from the expandable transapical introducer sheath, again checking to ensure that there is no hemorrhage from the valves or ports at the proximal end of the sheath. The sheath is removed from the patient in one of three ways. In some embodiments, the sheath is simply withdrawn from the patient without collapsing the sheath. In some embodiments, the sheath is withdrawn from the patient without actively collapsing the sheath but the sheath collapses slightly following removal of the interventional catheters to ease withdrawal. In other embodiments, the sheath is actively reduced in diameter or cross-section and is then withdrawn from the patient, according to methodology and apparatus disclosed herein. Hemostasis can be maintained using sutures as prescribed by standard hospital technique or by the application of a specialized myocardial access hemorrhage control device. Hemostasis and stabilizing balloons on the outside of the sheath can be used to minimize bleeding while the puncture site relaxes closed.

Prior art sheaths generally require a surgical incision into the ventricular myocardium through which the sheath is inserted into the ventricle, often with associated tearing of tissue.

The expandable transapical sheath has advantages over standard introducer sheaths in that it is inserted in its first, small diameter configuration, into a tissue puncture site, advanced to the target treatment location, and then dilated circumferentially to gently expand the myocardial tissue in an atraumatic fashion to a size capable of allowing passage of a cardiac valve prosthesis. Reduced tissue trauma, less blood loss, and improved healing of the myocardium are benefits of the expandable transapical sheath. In other embodiments of the procedure, the expandable transapical sheath can be inserted over a guidewire, through the pericardium, rather than through a pericardial incision, thus improving cardiac healing response and reducing adhesions associated with poor or incomplete pericardial closure following cardiac procedures.

Some of the main reasons for the malleable embodiments include control over cross-sectional shape, ability to embed the reinforcement in the polymer layers without needing to create some difficult to manufacture decoupling of the polymer and the reinforcement, the high strength of the sheath following placement, and prevention of lumen re-collapse caused by body tissue. The ability of this device to remodel to the desired shape to generate a superhighway for placement of implants and other medical devices is superior to anything available today. Furthermore, the device provides a relatively smooth interior lumen which allows passage of instruments and implants of very large size without excessive binding or friction. No other sheath exists today that has these benefits.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein. These and other objects and advantages of the present invention will be more apparent from the following description taken in conjunction with the accompanying drawings.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

FIG. 19A illustrates a side view of the expandable transapical sheath in its diametrically collapsed, first configuration or state, according to an embodiment of the invention;

FIG. 19B illustrates a side view of the expandable transapical sheath in its second, fully expanded configuration, according to an embodiment of the invention;

FIG. 19C illustrates a side view of a dilator configured for use with the expandable transapical sheath, according to an embodiment of the invention;

DETAILED DESCRIPTION OF THE ILLUSTRATED EMBODIMENTS

As used herein, a catheter or sheath can be described as an axially elongate structure having a proximal end, a distal end, and a lumen extending partially, or completely, therethrough. As used herein, the terms proximal and distal refer to directions or positions along a longitudinal axis of a catheter or medical instrument. Proximal refers to the end of the catheter or medical instrument closest to the operator, while distal refers to the end of the catheter or medical instrument closest to the patient. For example, a first point is proximal to a second point if it is closer to the operator end of the catheter or medical instrument than the second point. However, the terms anatomically proximal and anatomically distal refer to orientations within the body. For example, a point is more anatomically distal if it is further from the heart than a point described as anatomically proximal.

Figure 1:
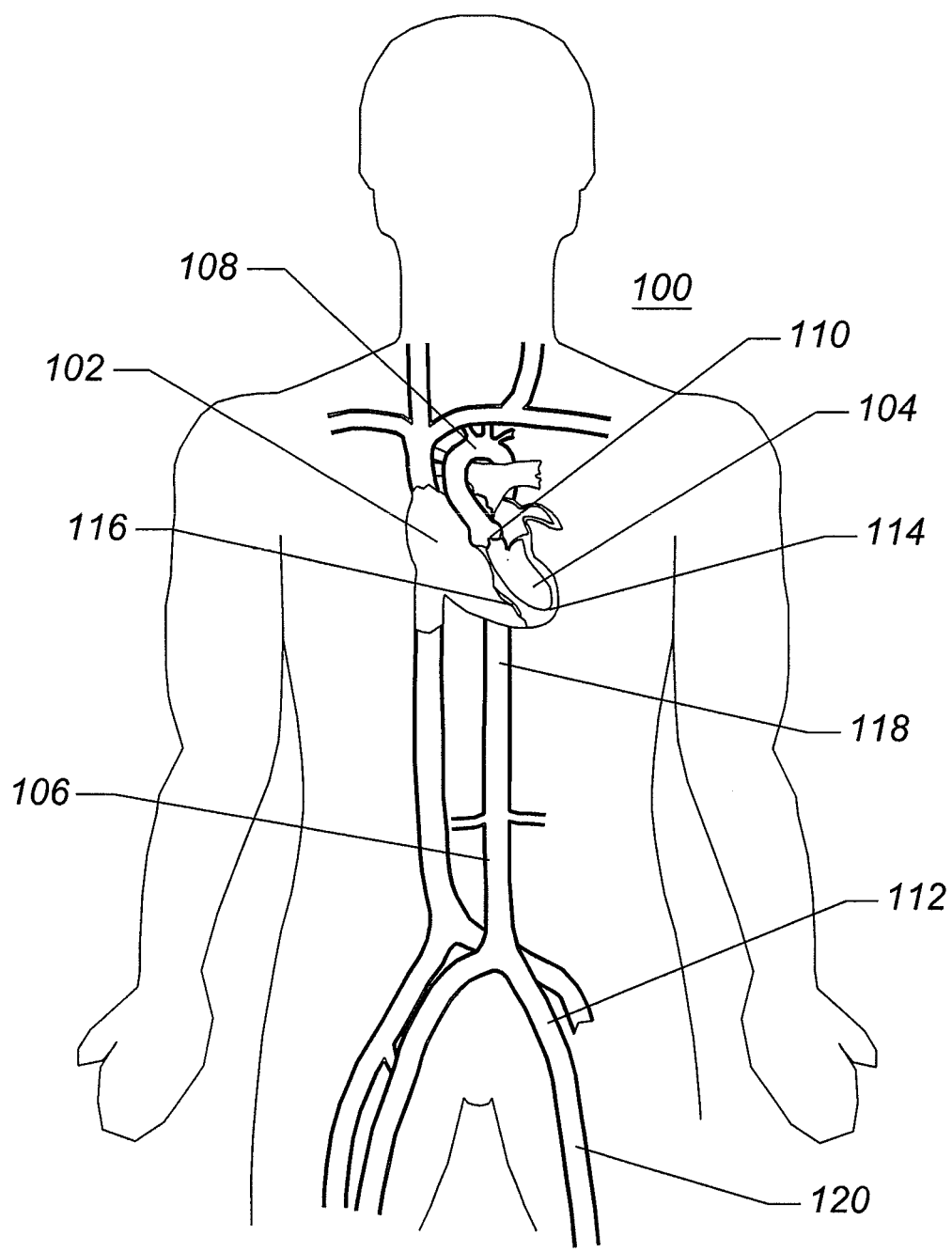
FIG. 1 is a front view schematic representation of the human circulatory system including the heart, the aorta, and the iliac arteries.

FIG. 1 is a schematic frontal (anterior) illustration (looking posteriorly) of a human patient 100 that illustrates components of the central circulation. As shown, the central circulation generally comprises comprising a heart 102, a left ventricle 104, a descending aorta 106, an aortic arch 108, an aortic heart valve 110, an iliac artery 112, a left ventricular apex 114, a right ventricle 116, a femoral artery 120, and a thoracic aorta 118. In this illustration, the left anatomical side of the body of the patient 100 is toward the right of the illustration. FIG. 1 primarily illustrates components of the central circulation.

Referring to FIG. 1, the heart 102 is a pump, the outlet of which is the aorta, including the aortic arch 108, the thoracic aorta 118, the descending aorta 106, which comprise the primary artery in the systemic circulation. The circulatory system, which is operably connected to the heart 102 further defined by a right and left heart, further comprises the return, or venous, circulation. The iliac arteries 112 are operably connected to, and receive blood from, the aorta. The femoral arteries 120, are operably connected to, and receive blood from, the iliac arteries 112. The veins carry blood from the tissues of the body back to the right heart, which then pumps the blood through the lungs and back into the left heart. Pressures within the venous circulation generally average 20 mm Hg or less. The arteries of the circulatory system carry oxygenated blood (not shown) from left ventricle of the heart 102 to the tissues of the body 100. The pressures within the aorta undulate, with a modified triangle waveform, between diastolic pressures of around 80 mm Hg to a systolic pressure of around 120 mm Hg. A hypotensive person may have arterial pressure lower than 120/80 mm Hg and a hypertensive person may have arterial pressures higher than 120/80 mm Hg. Systolic arterial pressures of about 300 mm Hg, or greater, can occur in extremely hypertensive persons.

Figure 2:
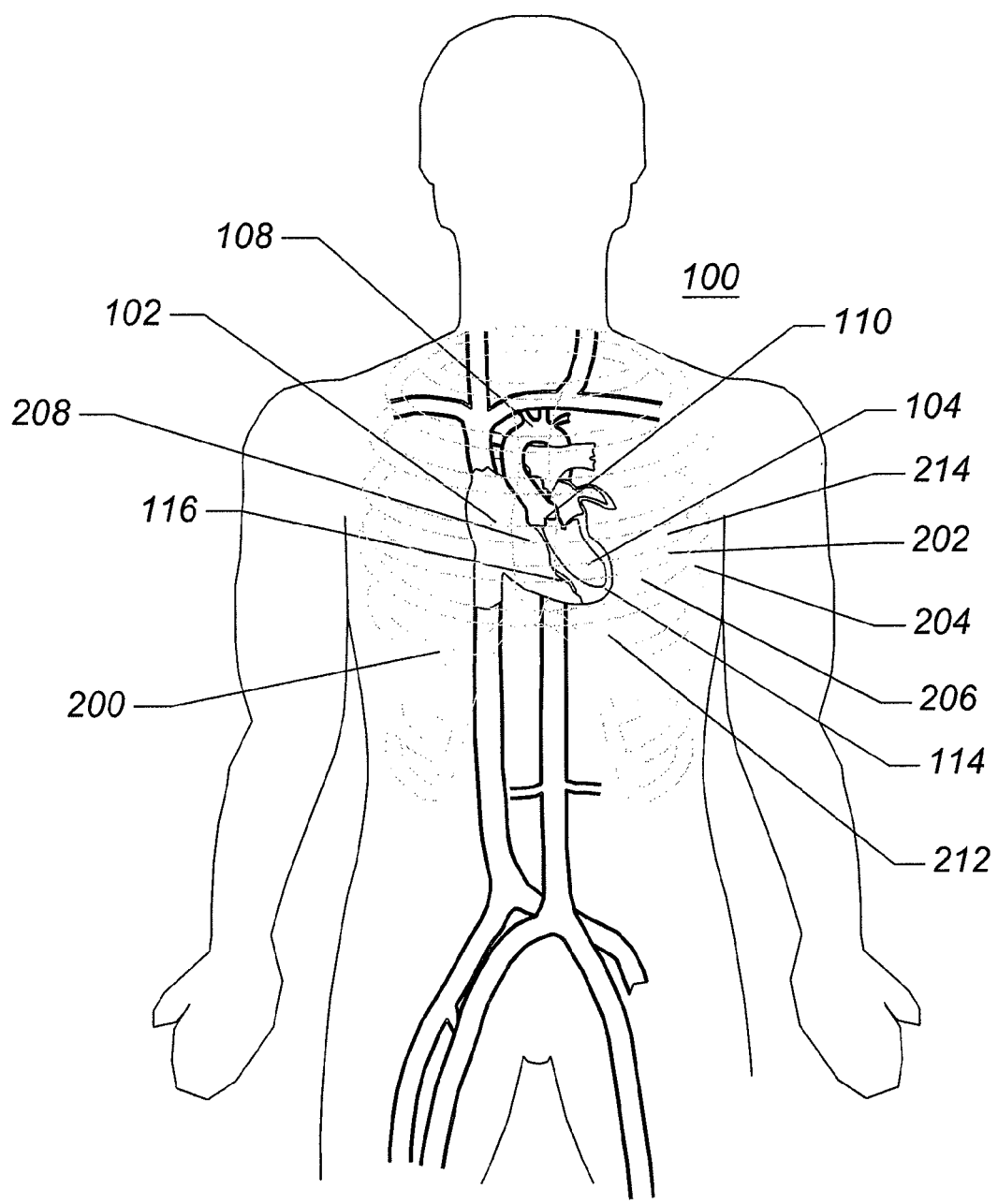
FIG. 2 is a front view schematic representation of the human circulatory system further showing the ribcage.

FIG. 2 is a schematic frontal illustration, looking posteriorly from the anterior side, of the patient 100. In this illustration, much of the left ventricle 104, left atrium, and the aortic outflow tract have been cut away to permit visibility of the aortic root structure and aortic valve 110, which lies on the posterior aspect of the heart 102. The sternum 208 is affixed to the ribcage 200, which is illustrated surrounding the heart 102, the left ventricle 104, the aortic arch 108, a left ventricular apex 114, the right ventricle 116, and the aortic valve 110. The fifth rib 202 lies above the ventricular apex 114 while the sixth rib 204 lies below the ventricular apex 114. The fifth intercostal space 206 generally lies directly over the ventricular apex 114 in a majority of patients, however, the sixth intercostal space 212, or the fourth intercostal space 214 can also provide access to the left ventricular apex 114 in some patients.

Referring to FIG. 2, access to the left ventricle 104 of the heart 102 of the patient 100 can be advantageously performed through the fifth 212 intercostal space. A port access, or alternatively an open surgical, procedure can be performed to gain access to the heart 102. The ribcage must be traversed but can also be used to reliably guide access to the heart 102.

Figure 3:
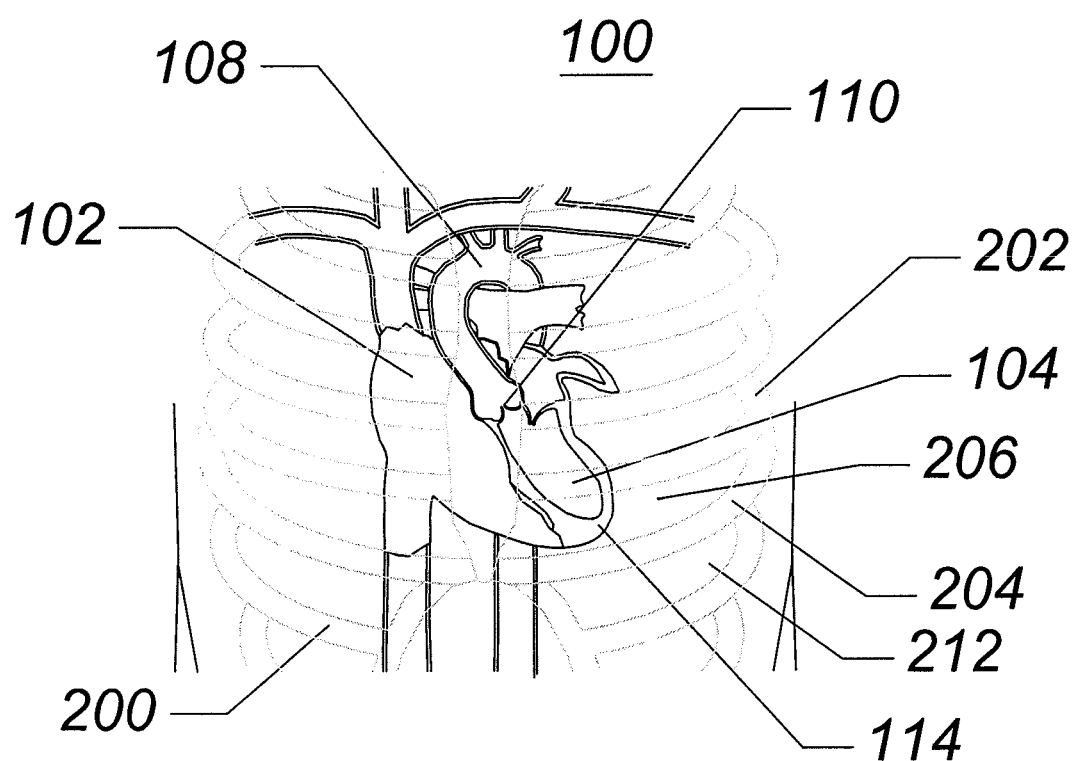
FIG. 3 illustrates a close-up of the thoracic region of a human showing the ribs and the heart, wherein the heart is shown in partial cutaway view.

FIG. 3 is a close-up view of the heart 102 within the rib cage 200. The rib cage 200 comprises the fifth rib 202 and the sixth rib 204. The rib cage 200 also defines the port known as the fifth intercostal space 206 as well as the fifth intercostal space 212. The aortic valve 110 and the aortic arch 108, as well as the left ventricle 104 and the ventricular apex 114 are visible beneath the rib cage 200.

Figure 4:
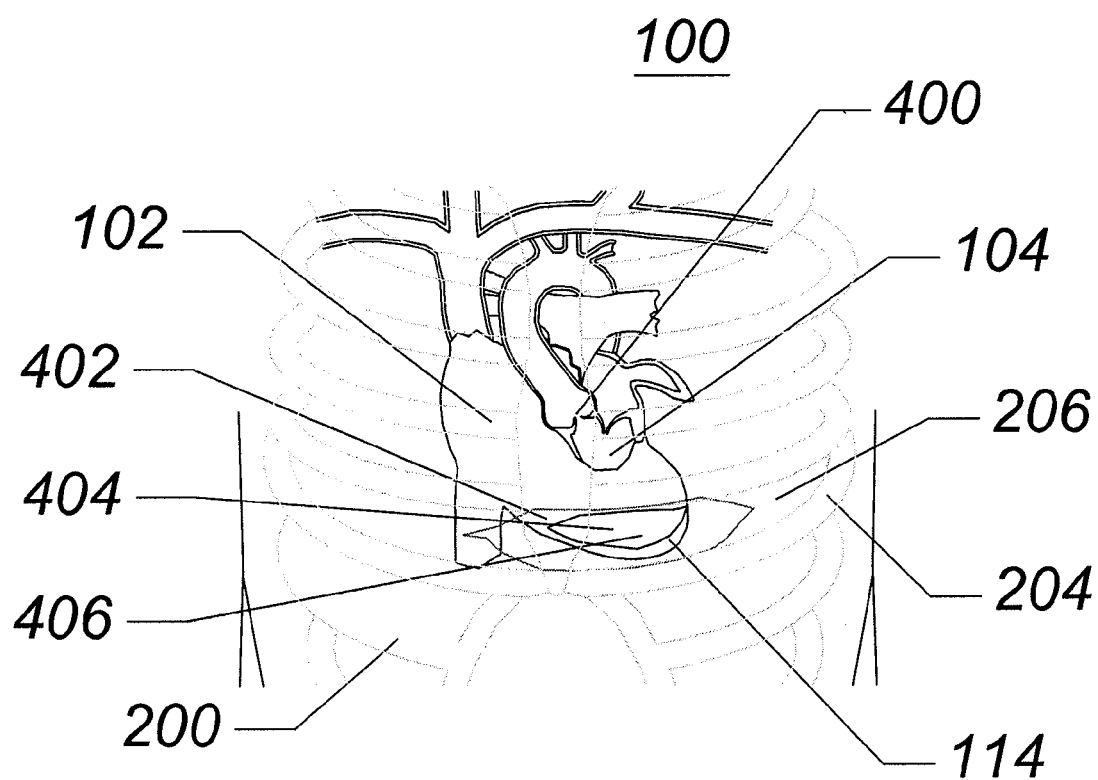
FIG. 4 illustrates a close-up of the thoracic region of a human showing the ribs and the heart, wherein incisions, or cutdowns, in both the skin and the pericardial covering of the heart have been completed, according to an embodiment of the invention.

FIG. 4 illustrates a close-up view of the heart 102 within the rib cage 200. An incision 402 has been made into the skin, fascia and underlying fat and muscle to expose the pericardium 404. An incision 406 has been made in the pericardium 404. The incisions are made through the fifth intercostal space 206 in the region of the ventricular apex 114. The heart 102 is shown in partial sectional view to reveal the left ventricle 104 and the aortic valve 400.

Figure 5:
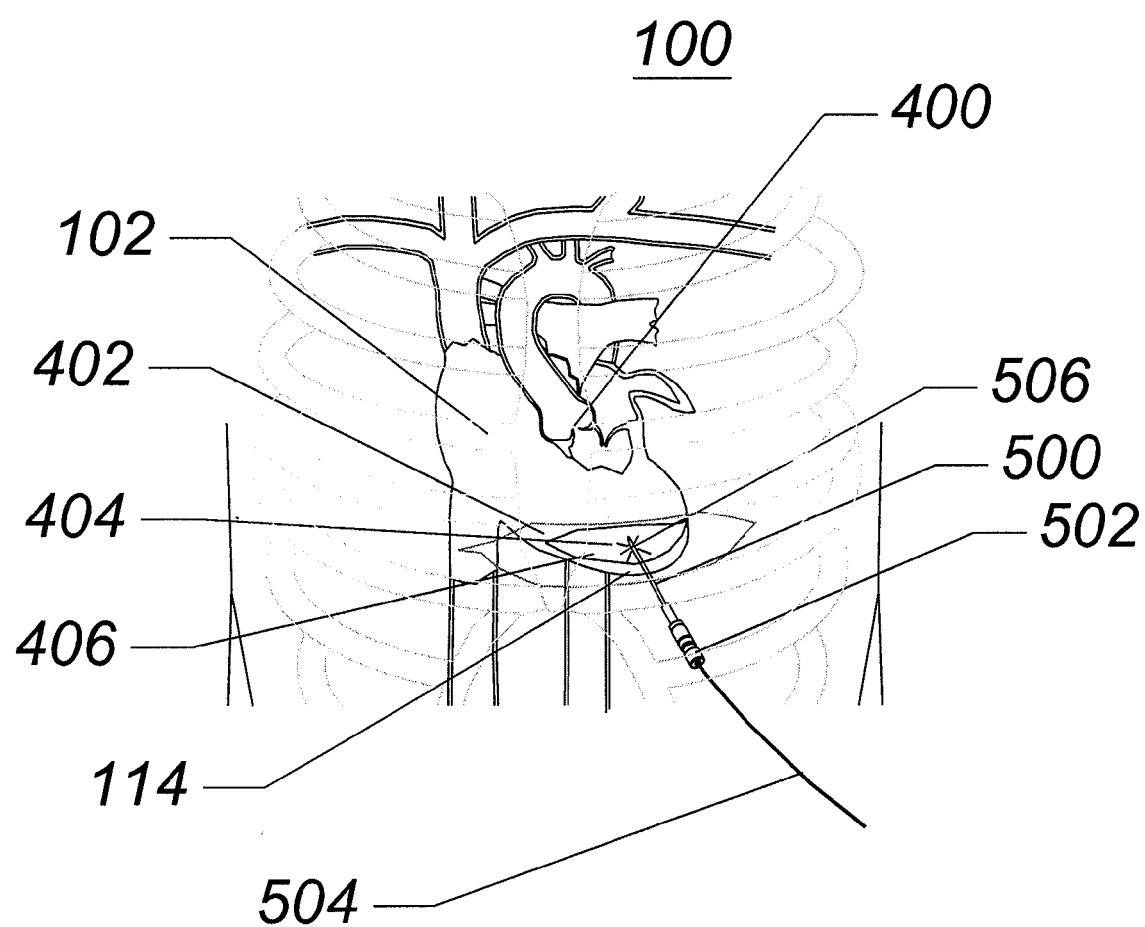
FIG. 5 illustrates a hollow needle and guidewire inserted into the ventricular apex of the heart through the access cutdown, according to an embodiment of the invention.

FIG. 5 illustrates a close-up view of the heart 102. The heart 102 is shown in partial sectional view to reveal the aortic valve 400. A hollow needle 500 has been inserted into a puncture site 506 in the ventricular apex 114, through the skin incision 402 and through the incision 406 in the pericardium 404. In other embodiments, the incision 406 in the pericardium 404 can be omitted with potentially beneficial results in terms of improved healing and reduced cardiac adhesions. The hollow needle 500 further comprises a hemostasis valve 502. The hemostasis valve 502 is affixed, or integral, to the proximal end of the hollow needle 500. The hemostasis valve is configured to seal against loss of blood at systemic blood pressure with nothing inserted through its lumen, or when a guidewire is inserted therethrough. A guidewire 504 has been inserted through the hemostasis valve 502, through the hollow needle 500 and into the left ventricle.

Figure 6:
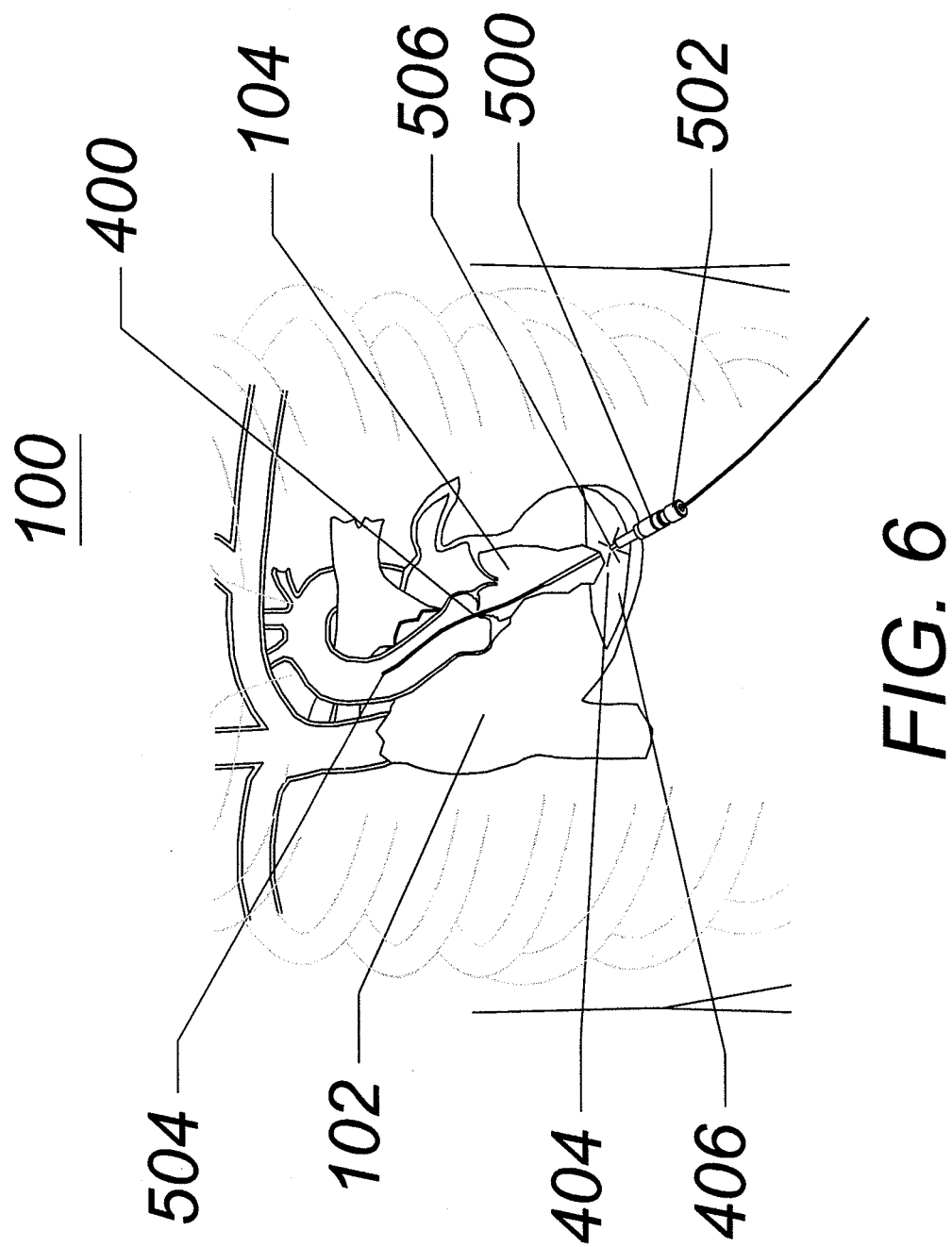
FIG. 6 illustrates the guidewire having been advanced through the aortic valve and into the aortic outflow tract with the hollow needle and a hemostasis valve still in place, according to an embodiment of the invention.

FIG. 6 illustrates a close-up view of the heart 102 of patient 100, wherein the guidewire 504 has been advanced through the left ventricle 104, through the aortic valve 400 into the aortic outflow tract. Rib and sternum detail has been deleted to improve visibility of the heart 102 structures. The incision 404 is illustrated in the pericardium 406. The hollow needle 500 is shown penetrating the ventricular apex at the puncture site 506. The hollow needle 500 can be a hypodermic needle, generally fabricated from stainless steel of other biocompatible metal with a metal or polymer hub, sized in the range of about 14 to 22 gauge with a preferable size of around 18 gauge. The guidewire 504 can range in diameter from 0.018 inches to 0.038 inches and can have standard, stiff, or extra-stiff flexibility characteristics. The length of the guidewire 504 should range between about 50-cm and 100-cm, such that a transapical sheath and catheter can be routed thereover while the distal end of the guidewire is securely placed within the aortic outflow tract and possibly as far as the aortic arch. The guidewire 504 is generally of sufficient length that the proximal portion of it extends outside the body. Thus, the guidewire is as long as, or longer than, twice the distance from the proximal portion of an inserted instrument or catheter to the treatment site in the patient 100. Guidewires can be PTFE coated to improve lubricity and can have various types of tip configurations including, but not limited to, straight, "J", floppy tip, rigid tip, and the like.

The central arterial circulation, through which the guidewire 504 has been routed, may range from 60 to over 300 mm Hg depending on the level of hypertension or hypotension existent in the patient. By accessing the heart through the arterial circulation, the chance of hemorrhage, or blood leakage, from the catheter or sheath insertion site is minimized by use of hemostasis valves built into, or affixed to, any catheters, sheaths, hollow needles, or introducers used on the patient. The hemostasis valve 502 is illustrated coupled to the proximal end of the hollow needle 500. The hemostasis valve 502 can be bonded, welded, bayonet mounted, screwed, or otherwise affixed to the hollow needle 500 while maintaining fluid connectivity or operable connectivity between the lumen of the hollow needle and the lumen of the hemostasis valve 502.

Figure 7:
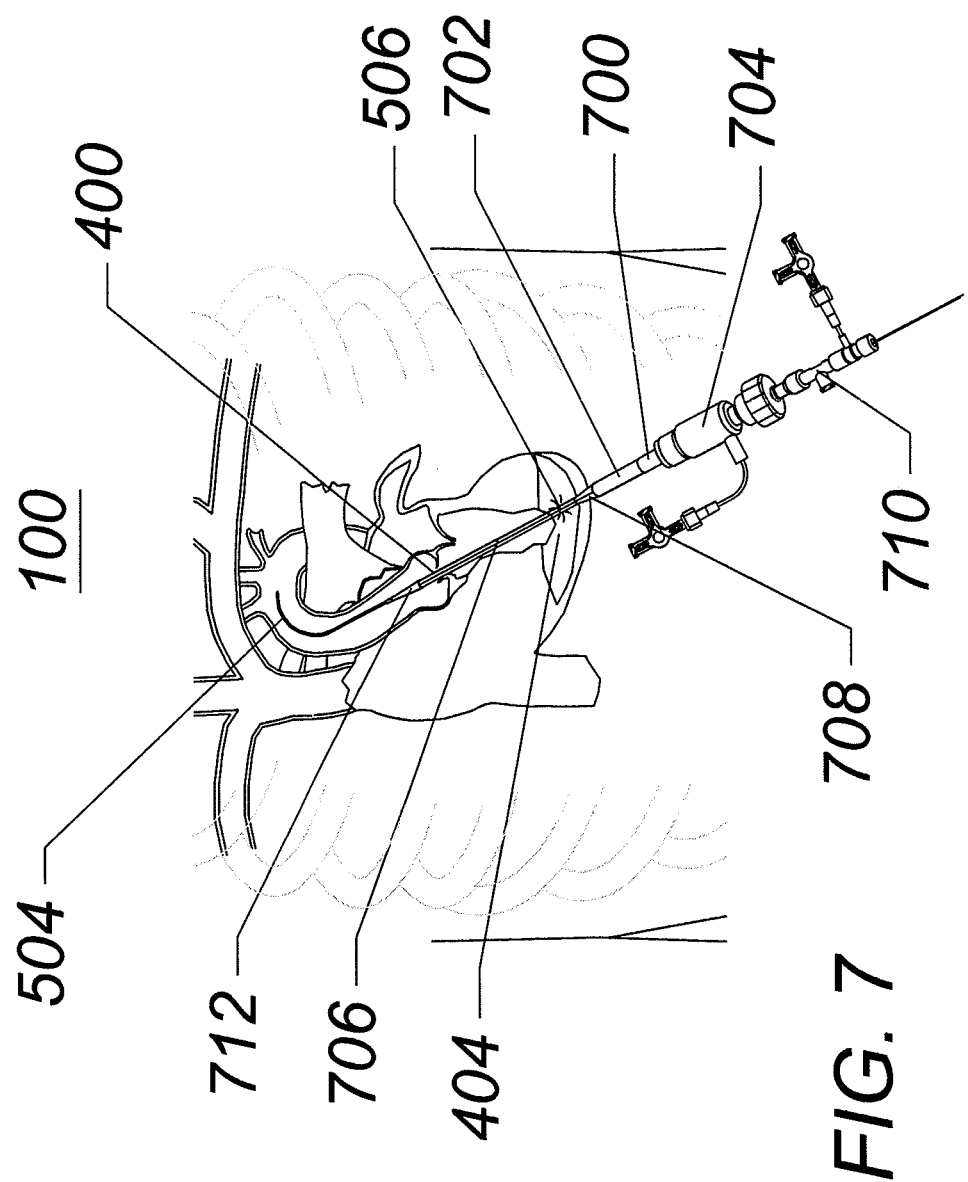
FIG. 7 illustrates an expandable transapical introducer sheath, in its first, radially collapsed configuration, advanced into the left ventricle, following the path of the previously placed guidewire through the ventricular myocardium of a patient, according to an embodiment of the invention.

FIG. 7 illustrates an expandable transapical sheath 700 inserted over the guidewire 504, following removal of the hollow needle 500 (reference FIGS. 5 & 6) in the patient 100. The expandable transapical sheath 700 has been inserted through the puncture site 506 exposed on the left ventricular myocardium by the pericardial incision 404. The expandable transapical sheath 700 is illustrated with its expandable distal end 706 in its first, radially, or diametrically, collapsed configuration. The expandable transapical sheath 700 comprises a sheath hub 704, a proximal non-expandable region 702, a distal expandable region 706, a transition zone 708, and a dilator 710. The dilator 710 further comprises a distal fairing tip 712. A central lumen (not shown) within the dilator 710, and extending entirely within and through the proximal and the distal end of the dilator 710, is slidably disposed over the guidewire 504. The sheath hub 704 is affixed, or integral, to the proximal end of the proximal tubing 702. The distal end of the proximal tubing 702 is affixed to the proximal end of the transition zone 708. The distal end of the transition zone 708 is affixed to the proximal end of the distal expandable region 706. The distal expandable region 706, in the illustrated embodiment, comprises a longitudinal fold along substantially its entire length. The distal expandable region 706 can comprise between 1 and 10 folds with a preferred range of 1 to 4. Each fold comprises at least an outside edge and an inside edge. The transition zone 708 retains a generally tapered configuration with the larger diameter proximally and the smaller diameter distally oriented. The transition zone 708 generally comprises the tail of the folds in the distal expandable region 706, said folds generally trailing off to nothing at or near the distal end of the transition zone 708. The distal expandable region 706 projects through the natural aortic valve 400, which is due for replacement but could, in certain situations or embodiments, be located just upstream of the aortic valve 400.

Figure 8:
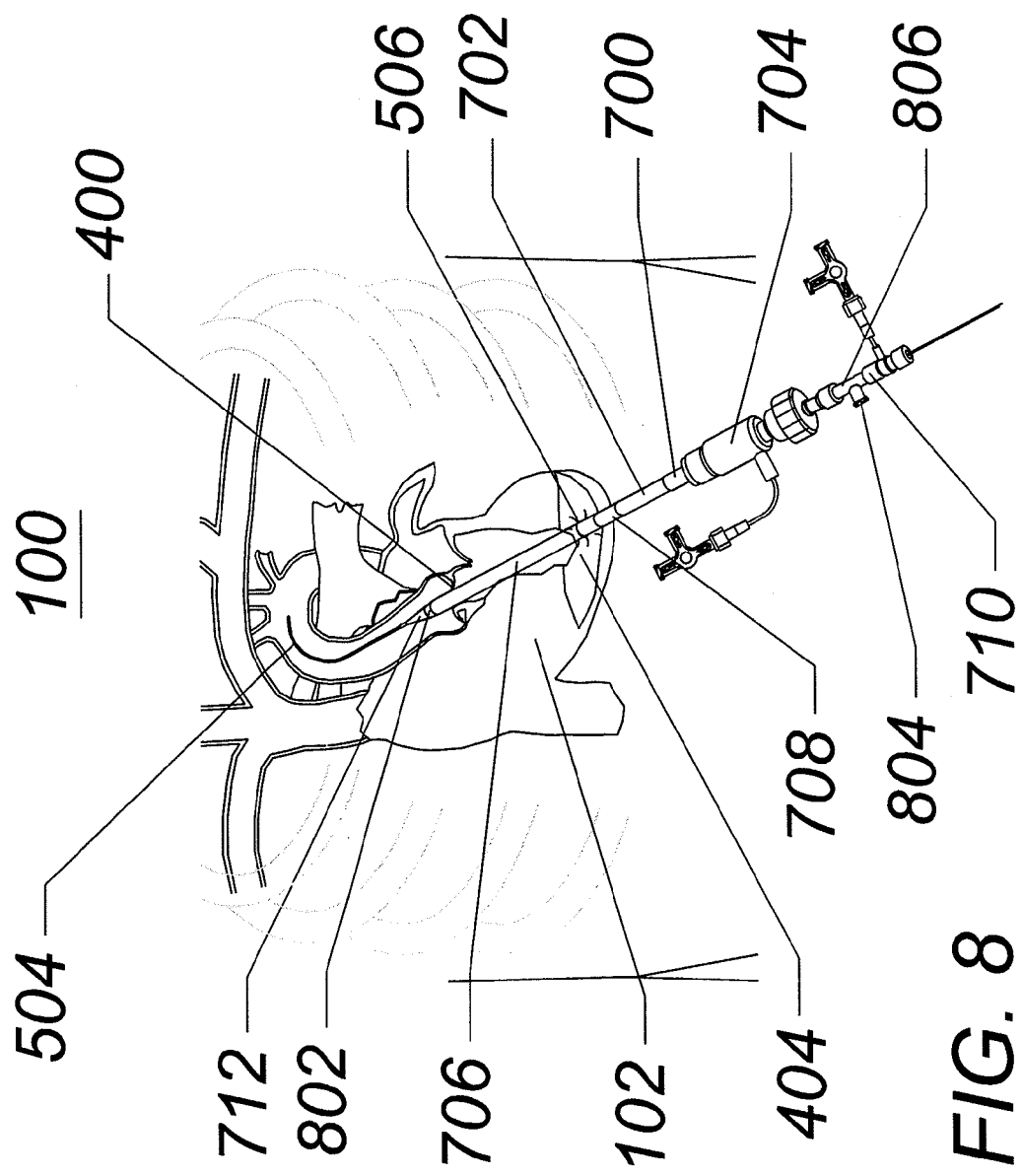
FIG. 8 illustrates the expandable transapical introducer sheath having been dilated to its fully expanded, second configuration, wherein the dilator remains in place, according to an embodiment of the invention.

FIG. 8 illustrates the expandable transapical sheath 700 with its distal, expandable region 706 having been diametrically expanded by forcible pressurization of a balloon 802 comprised by the dilator 710. The internal volume of the balloon 802 is operably connected to an inflation port 804 on a hub 806 of the dilator 710 by means of an inflation lumen (not shown) within the tubing (not shown) of the dilator 710. The distal fairing 712 is affixed to the dilator tubing (not shown) near the distal end of the fairing 712 but not at the proximal end of the fairing. The distal fairing 712 is elastomeric and expands diametrically with the balloon 802 while at the same time retracting distally toward the point where it is affixed to the dilator shaft (not shown). The puncture site 506 in the myocardium is expanded and seals against the expanded distal region 706 to prevent loss of blood from the pumping heart 102. The balloon 802 can be inflated with air, water, saline, radiographic dye contrast media, or the like. The pressure suitable for balloon inflation can range between 5 and 30 atmospheres, with a preferred range of 10 to 25 atmospheres.

Referring to FIG. 8, the transition zone 708 is no longer tapered but is generally cylindrical and reflects an approximately constant diameter extending the entire length of the internal lumen (not shown) of the expanded transapical sheath 700. The proximal, non-expandable region 702 retains generally the same shape as prior to expansion of the distal region 706. The distal end 706 of the transapical sheath 700 resides in the aortic outflow tract distal to the aortic valve 400.

Figure 9:
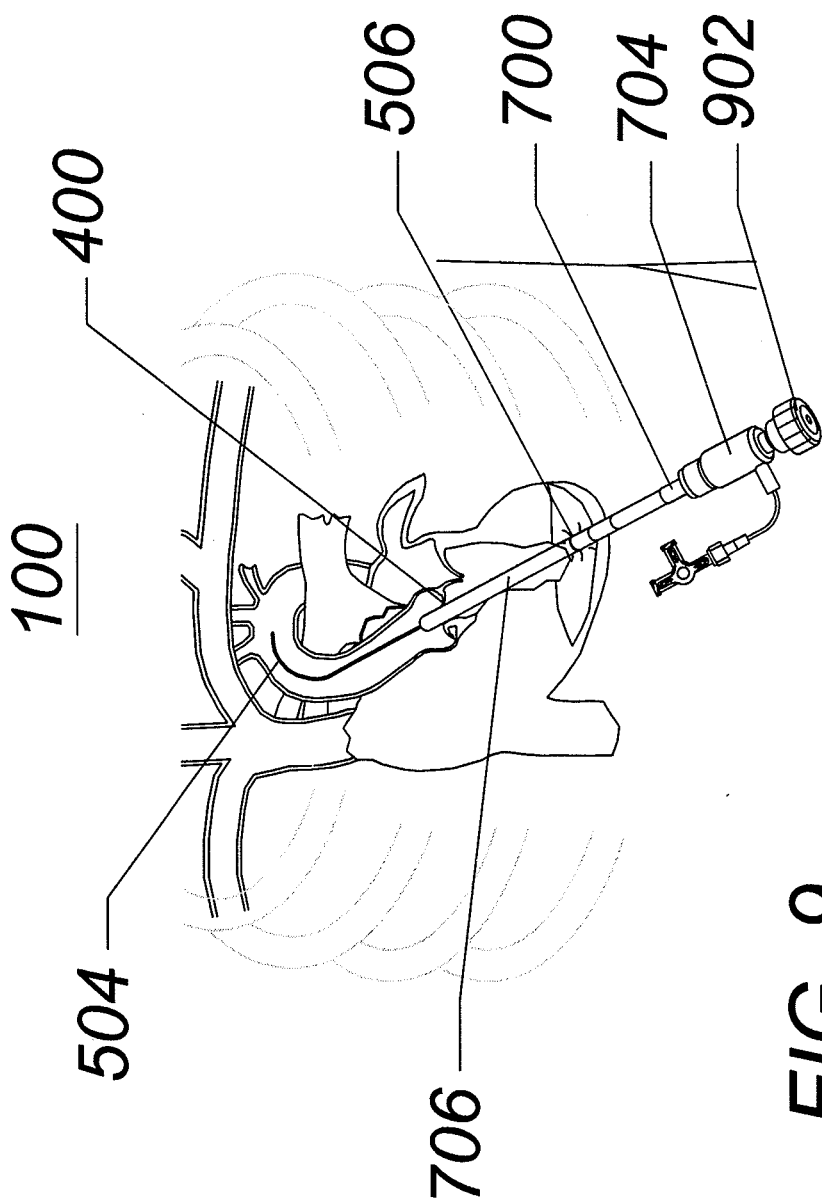
FIG. 9 illustrates the expandable transapical introducer sheath with its dilator having been deflated and removed from the lumen of the introducer sheath, according to an embodiment of the invention.

FIG. 9 illustrates the expandable transapical sheath 700 wherein the dilator 710 (refer to FIGS. 7 and 8) has had its balloon 802 deflated and the entire dilator 710 removed from the sheath 700. The distal region 706 remains fully expanded even though the support of the dilator 710 has been eliminated. Hemostasis valves 902 comprised within, or affixed to, the sheath hub 704 prevent loss of blood. The hemostasis valves 902 can comprise duckbill valves, pinhole valves, slit valves, ring-gaskets, Tuohy-Borst valves, or a combination thereof. The puncture site 506 remains sealed against blood loss or air entry into the cardiovascular system. The guidewire 504 remains in place and is still routed into the aortic arch, although it can optionally be removed from the system. Note that the aortic valve 400 is illustrated as being heavily calcified with reduced leaflet motion, a propensity for stenosis, and a propensity for incompetence.

Figure 10:
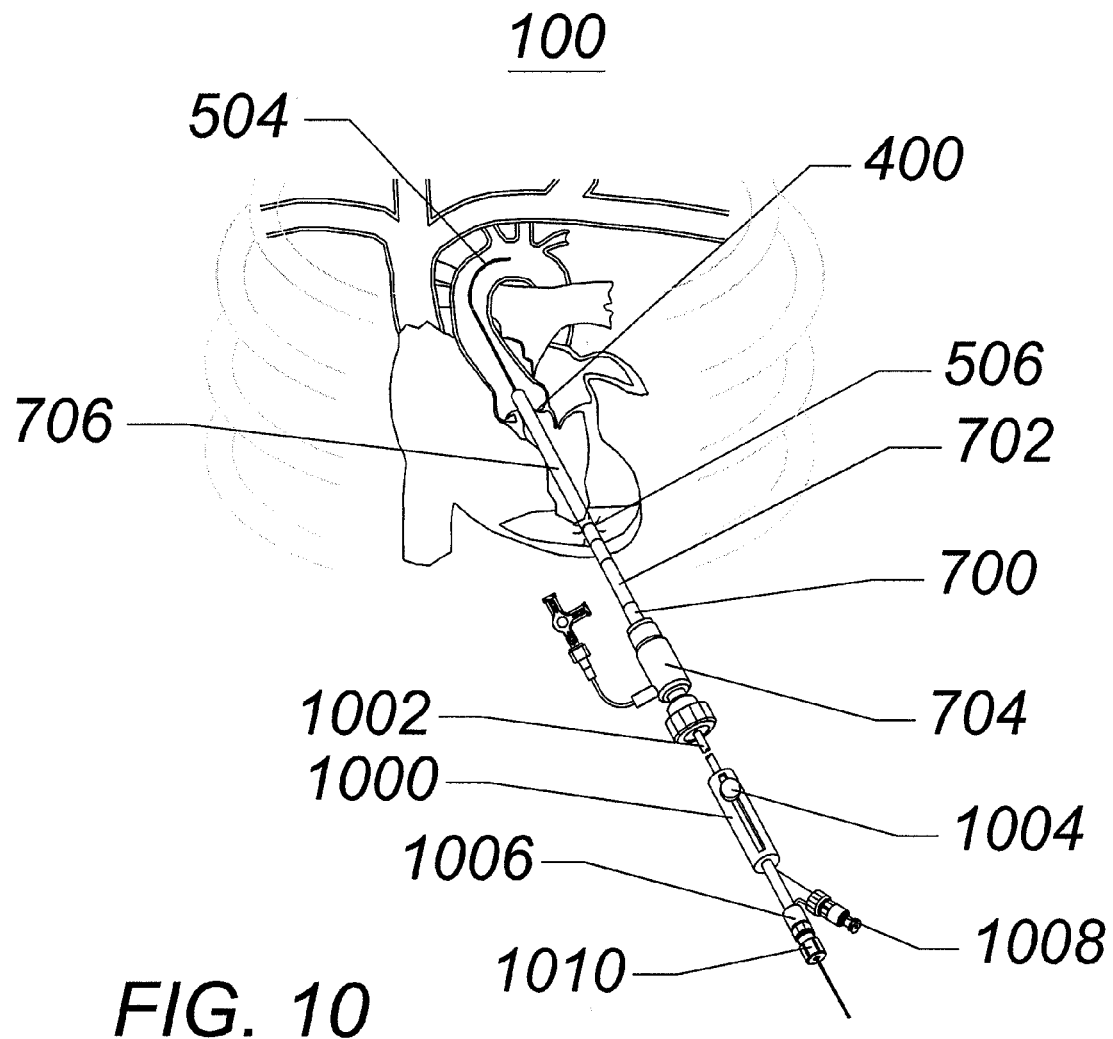
FIG. 10 illustrates an aortic valve delivery catheter introduced into the lumen of the expanded transapical introducer sheath through a proximal hemostasis valve, according to an embodiment of the invention.

FIG. 10 illustrates a patient 100 wherein an aortic valve delivery catheter 1000 has been inserted through the expandable transapical sheath 700. The transapical sheath 700 comprises the sheath hub 704, the proximal tubing region 702, and the distal tubing region 706. The guidewire 504 remains in place. The aortic valve delivery catheter 1000 further comprises a delivery catheter shaft 1002, a delivery catheter hub 1006, a valve deployment slider 1004, a valve expansion port 1008, and a central port hemostasis valve 1010. The sheath 700 remains in place in the puncture site 506 in the ventricular myocardium. The distal expandable region 706 projects through the natural aortic valve 400, which is diseased or damaged due to calcification, regurgitation, stenosis, or other pathologies, and needs replacement.

Figure 11:
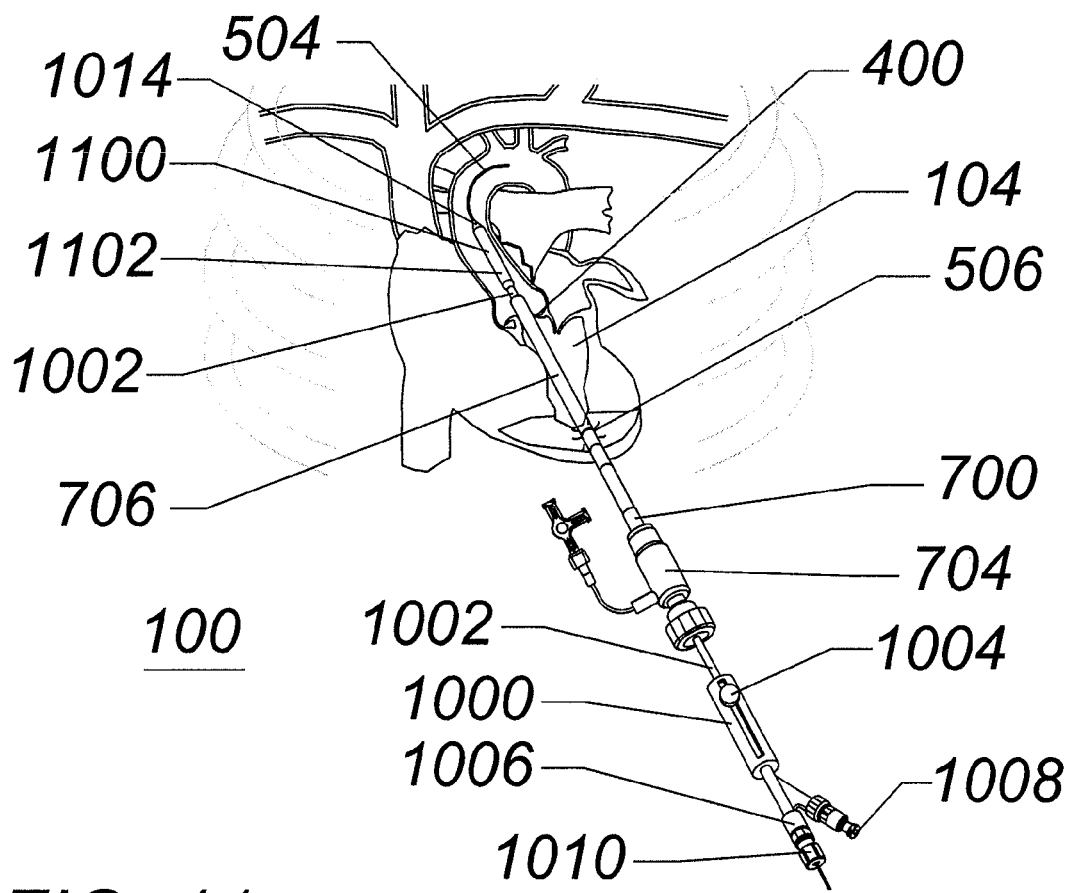
FIG. 11 illustrates the expanded transapical sheath with the aortic valve delivery catheter having been introduced therethrough into the aortic outflow tract, with an expansion restrictor and shield in place over the valve, according to an embodiment of the invention.

FIG. 11 illustrates a patient 100 with the aortic valve delivery catheter 1000 having been advanced out the distal end 706 of the transapical expandable sheath 700. The aortic valve delivery catheter 1000 further comprises a prosthetic aortic valve 1100, a distal valve shroud 1102, the delivery catheter tubing 1002, the delivery catheter hub 1006, the valve deployment slider 1004, the inflation sidearm 1008, the delivery catheter nose cone 1014, and the delivery catheter central hemostasis valve 1010. The guidewire 504 remains in place through the valve delivery catheter 1000. The valve deployment slider 1004 is advanced distally in its first, introduction position and the distal valve shroud 1102 fully surrounds and encloses the prosthetic aortic valve 1100 (not visible). The distal region 706 projects through the natural aortic valve root 400. The proximal region 702 of the expandable transapical sheath 700 is affixed to the sheath hub 704. The distal region 706 projects through the apical puncture site 506 and into the left ventricle 104.

Figure 12:
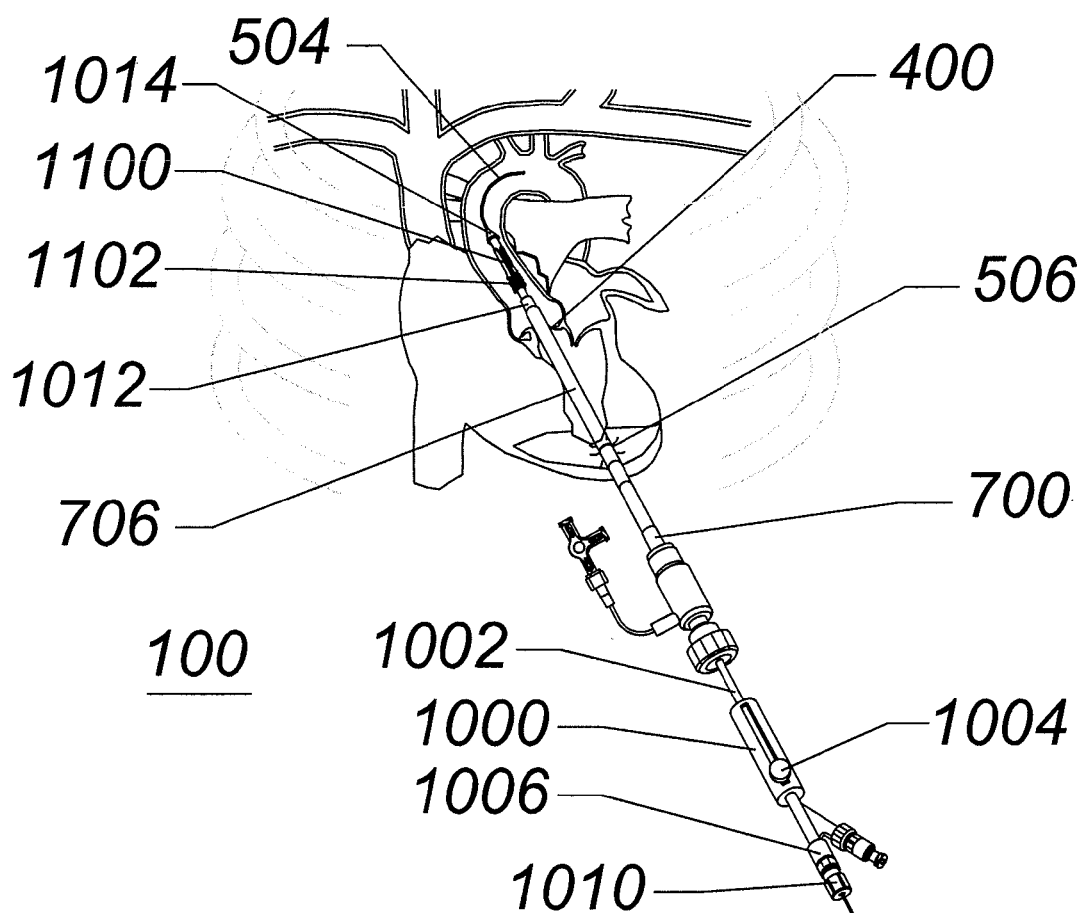
FIG. 12 illustrates the aortic valve delivery catheter with the expansion restrictor and shield retracted to expose the valve prosthesis within the aortic root, according to an embodiment of the invention.

FIG. 12 illustrates a patient 100 with the aortic valve delivery catheter 1000 having been advanced out the distal end of the expandable transapical sheath 700. Retraction of the valve deployment slider 1004 in the proximal direction, causes the distal valve shroud 1012 to retract proximally, thus exposing the valve prosthesis 1100 inside the aortic root. The aortic valve prosthesis 1100 remains affixed to the delivery catheter shaft 1002. The aortic valve prosthesis 1100 is diametrically collapsed in its first, delivery configuration. The valve prosthesis 1100 further comprises a plurality of collapsed, flexible valve leaflets, and a diametrically collapsed valve fixation stent 1102. The distal valve shroud 1012, operably connected to the valve deployment slider 1004 by a linkage (not shown) running therebetween and connected thereto, remains slightly visible distal to the distal end of the expandable transapical sheath distal tubing 706. A nose cone 1014, affixed to the distal end of the valve deployment catheter 1000, remains in place but no longer covers and shields the distal end of the valve shroud 1012. The hemostasis valve 1010, affixed to the delivery catheter hub 1006, fluidically seals around the guidewire 504 to prevent blood loss or air intake into the valve deployment catheter 1000. The sheath distal expandable region 706 projects through the natural aortic valve root 400 as well as the apical puncture site 506. The guidewire 504 projects out through the hemostasis valve 1010, affixed to, and having a central lumen (not shown) operably connected to the central lumen of, the catheter hub 1006.

Figure 13:
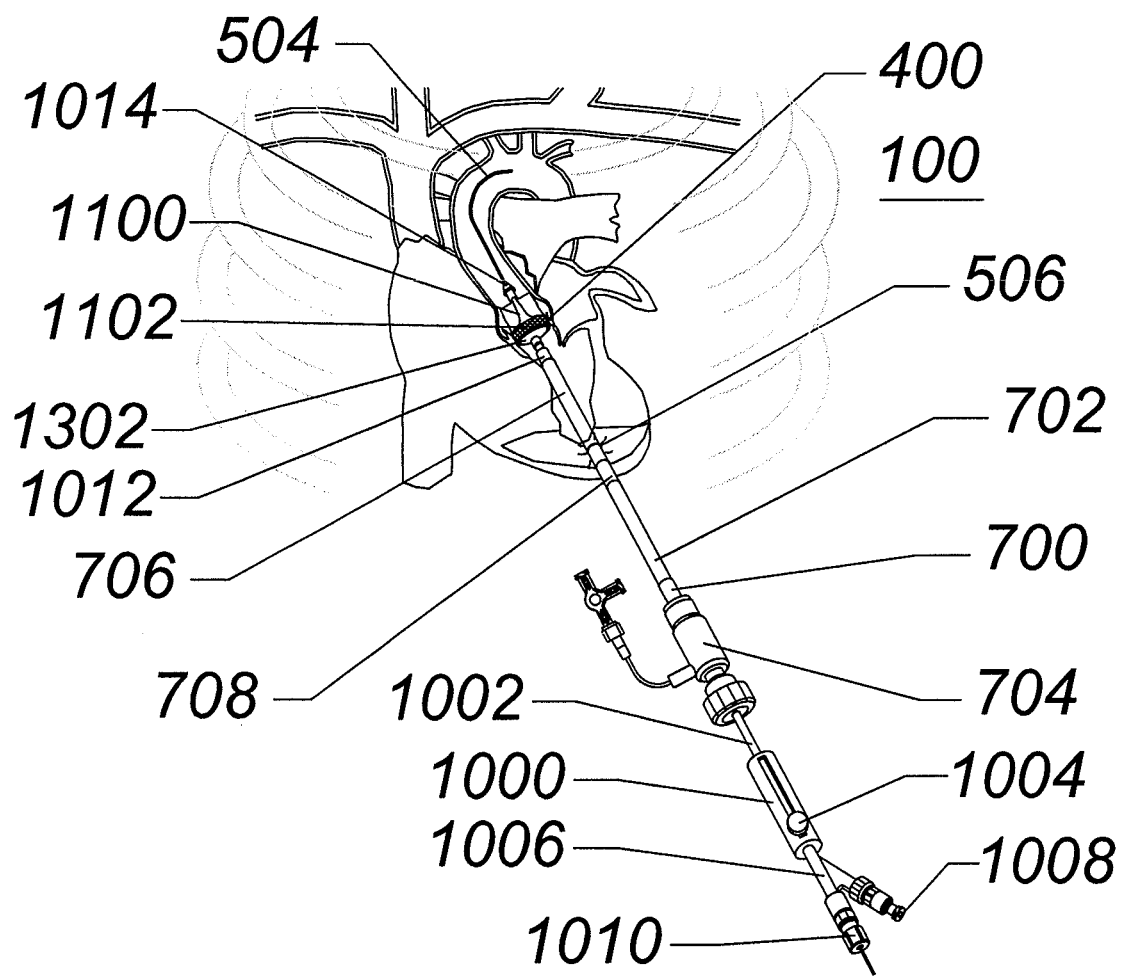
FIG. 13 illustrates inflation of a balloon dilator disposed, inside the valve prosthesis, and affixed to the valve delivery catheter, causing the valve prosthesis to expand and embed itself within the aortic root, according to an embodiment of the invention.

FIG. 13 illustrates a patient 100 with an expanded transapical sheath 700 inserted through the puncture site 506. The cardiac valve delivery catheter 1000 is inserted through the hemostasis valves in the hub 704 of the sheath 700 and the catheter 1000 and sheath 700 have been withdrawn proximally to align the valve prosthesis 1100, and specifically the valve fixation stent 1102, within the annulus of the natural, diseased aortic valve 400. A dilatation balloon 1302, affixed to the tubing 1002 of the valve delivery catheter 1000 has been expanded diametrically by pressurization with liquid through the catheter balloon inflation port 1008, affixed to the catheter hub 1006. The valve shroud 1012 is retracted proximally to allow expansion and deployment of the valve prosthesis 1100. The guidewire 504 is illustrated with its distal end within the aortic arch and the delivery catheter nose cone 1014 remains positioned just distal to the valve prosthesis 1100.

The valve shroud 1012 and the valve deployment slider 1004, and associated linkages (not shown) are optional and may be omitted in certain embodiments, if other provisions are made to maintain the valve 1100 in its first, smaller diameter during deployment. The dilatation balloon 1302 and the inflation port 1008 are also optional and can be eliminated if a self-expanding fixation stent 1102 is used, rather than the malleable fixation stent 1102 illustrated herein. In the embodiment where a self-expanding stent 1102 is used, a dilatation balloon 1302 could still be used, however, to enhance fixation between the stent 1102 and the aortic valve 400.

Referring to FIG. 13, the nose cone 1014 is illustrated affixed to the distal end of the catheter tubing 1002 with the guidewire 504 extending therebeyond. The nose cone 1014 comprises a central lumen, operably in communication with the central lumen of the catheter tubing 1002. The distal, expandable region 706 of the sheath remains fully dilated as does the transition zone 708. The proximal region 702 of the sheath 700 remains sealed to the puncture site 506 and hemorrhage is prevented thereby. The distal expandable region 706 is illustrated fully expanded.

The balloon 1302, a generally non-elastomeric but flexible bag-like structure, can be fabricated from materials such as, but not limited to, polyester, polyimide, polyamide, reinforced polymers, or the like, using stretch blow molding fabrication techniques. The balloon 1302 can have a wall thickness ranging from 0.0005 inches to 0.005 inches with a preferred range of 0.0008 to 0.003 inches. The diameter of the balloon 1302 is advantageously sized to approximately match, or be slightly larger than, the expected implantation diameter of the natural aortic valve annulus 400 less the thickness of the valve prosthesis 1100 and fixation stent 1102 structure. The ends of the balloon 1302 can be affixed to the catheter shaft 1002 using heat welding or gap filling seals, adhesives, or the like. Similar fabrication techniques are also used for the balloon on the dilator 710 (See FIG. 7) of the sheath 700. In its non-expanded state, the balloon 1302 is folded or wrapped tightly around the catheter shaft 1002. In other embodiments, the balloon 1302 can be eliminated from the system. The valve fixation stent 1102, in this embodiment, can comprise elastomeric elements, superelastic elements, shape memory elements, or a combination thereof. The valve fixation stent 1102 can be a self-expanding structure that is constrained by a sleeve or other restraint 1012, until which time the restraint 1012 is controllably removed or retracted by the operator by action applied at the proximal end of the valve delivery catheter 1000. Following removal of the restraint, the valve fixation stent 1102 expands in a direction lateral to the longitudinal axis of the valve delivery catheter. The valve fixation stent 1102 can comprise waffle patterns, hooks, barbs, cleats, screws, claws, or other structures to ensure embedment within the natural valve annulus. A separate, optional, balloon assist can still be used with the self-expanding stent to enhance seating of the valve prosthesis 1100.

Figure 14:
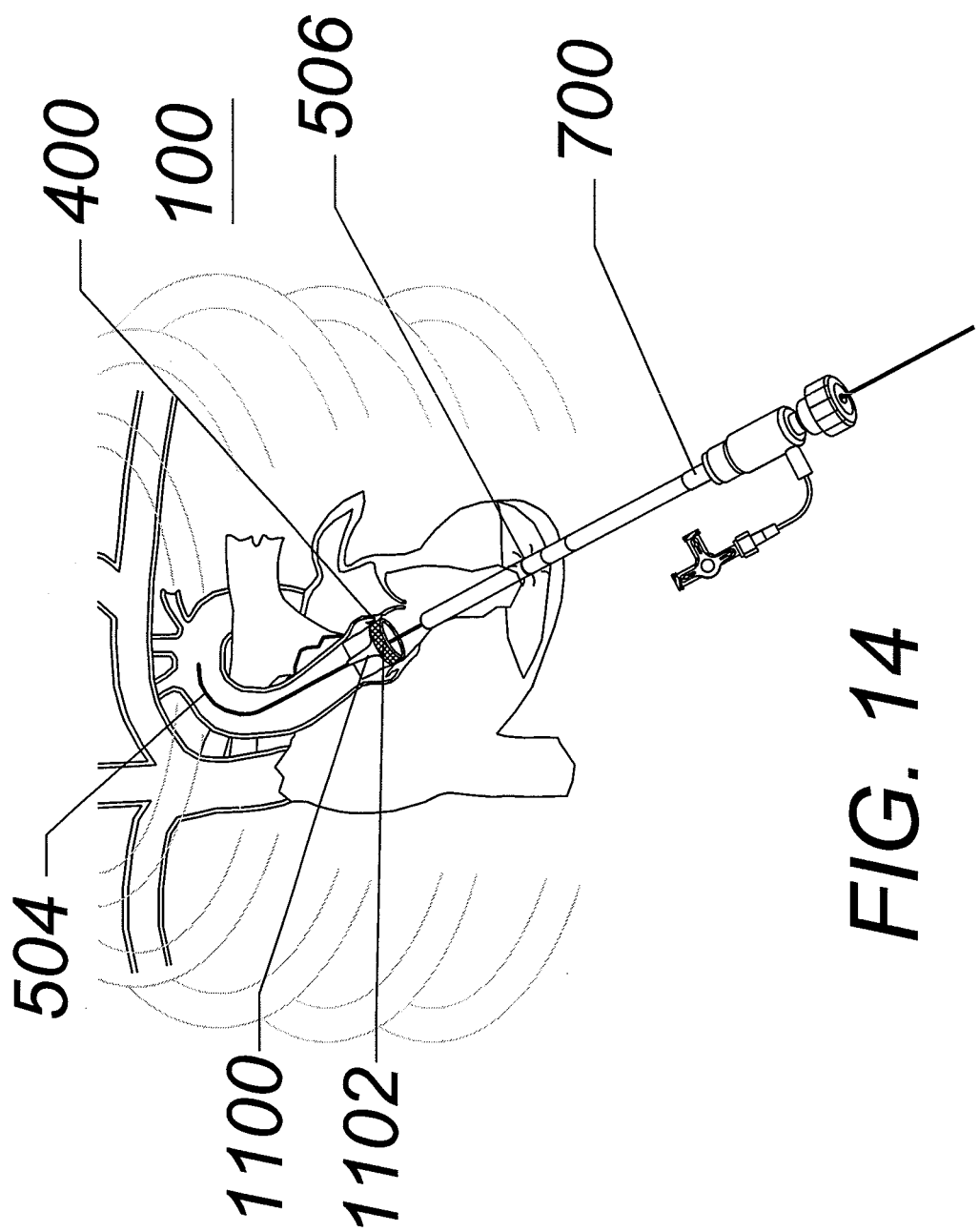
FIG. 14 illustrates removal of the valve delivery catheter with the expandable transapical sheath, guidewire, and valve prosthesis still in place, according to an embodiment of the invention.

FIG. 14 illustrates the patient 100 with the valve prosthesis 1100 secured in place within the natural aortic valve annulus 400 by the fixation stent 1102. The valve deployment catheter of FIGS. 10 to 13 has been removed leaving only the guidewire 504 in place. The expanded transapical sheath 700 remains in place at this point in the procedure and seals to the puncture site 506 in the left ventricular apex.

Figure 15:
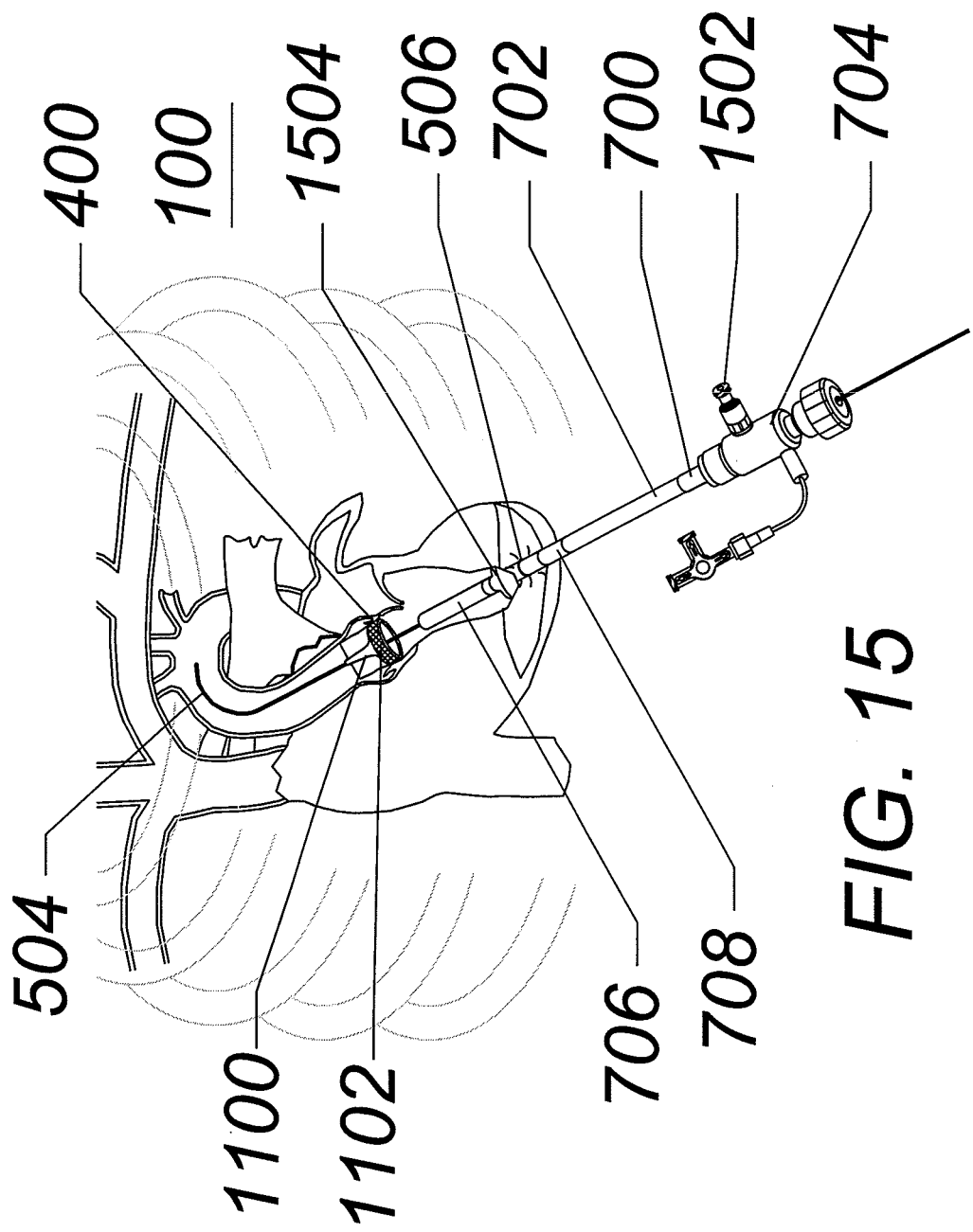
FIG. 15 illustrates an internal stabilization balloon affixed to the expandable transapical sheath, wherein the stabilization balloon is inflated within the left ventricle and positioned adjacent the entrance site, according to an embodiment of the invention.

FIG. 15 illustrates another embodiment of the expandable transapical sheath 700 wherein the sheath 700 further comprises a fixation balloon 1504 affixed to the expandable distal region 706. The fixation balloon 1504 can also be affixed to the non-expandable proximal region 702. The sheath hub 704 further comprises a balloon inflation port 1502, operably connected to the interior of the fixation balloon 1504 by way of inflation lumens within the wall of the sheath tubing 702, 706, and 708. The balloon inflation port 1502 is preferably terminated by a female Luer lock fitting which will accept connections to a commercial inflation device, generally a syringe with a threaded plunger assembly. The fixation balloon 1504 is advantageously fabricated from elastomeric materials and is a generally low-pressure balloon. The fixation balloon 1504 can be fabricated from polyurethane, silicone elastomer, thermoplastic elastomer, or the like. The relaxed wall thickness of the fixation balloon 1504 can range between 0.005 to 0.010 inches and preferably between 0.001 and 0.005 inches. The rated inflation pressure of the fixation balloon 1504 is generally two atmospheres or less. By pulling the fixation balloon 1504 retrograde, or proximally, against the left ventricular wall, the puncture site 506 can have its seal against the sheath 700 enhanced. Furthermore, the fixation balloon 1504 helps to stabilize the sheath 700 and prevent inadvertent retrograde dislodgement. When removal is desired, the fixation balloon 1504 can be deflated to remove the sheath 700 from the heart. A prosthetic valve 1100 is illustrated fixed in place within the aortic valve 400 annulus by the fixation stent 1102. The guidewire 504 is illustrated in place within the aortic arch but could also be removed by this point in the procedure.

Figure 16:
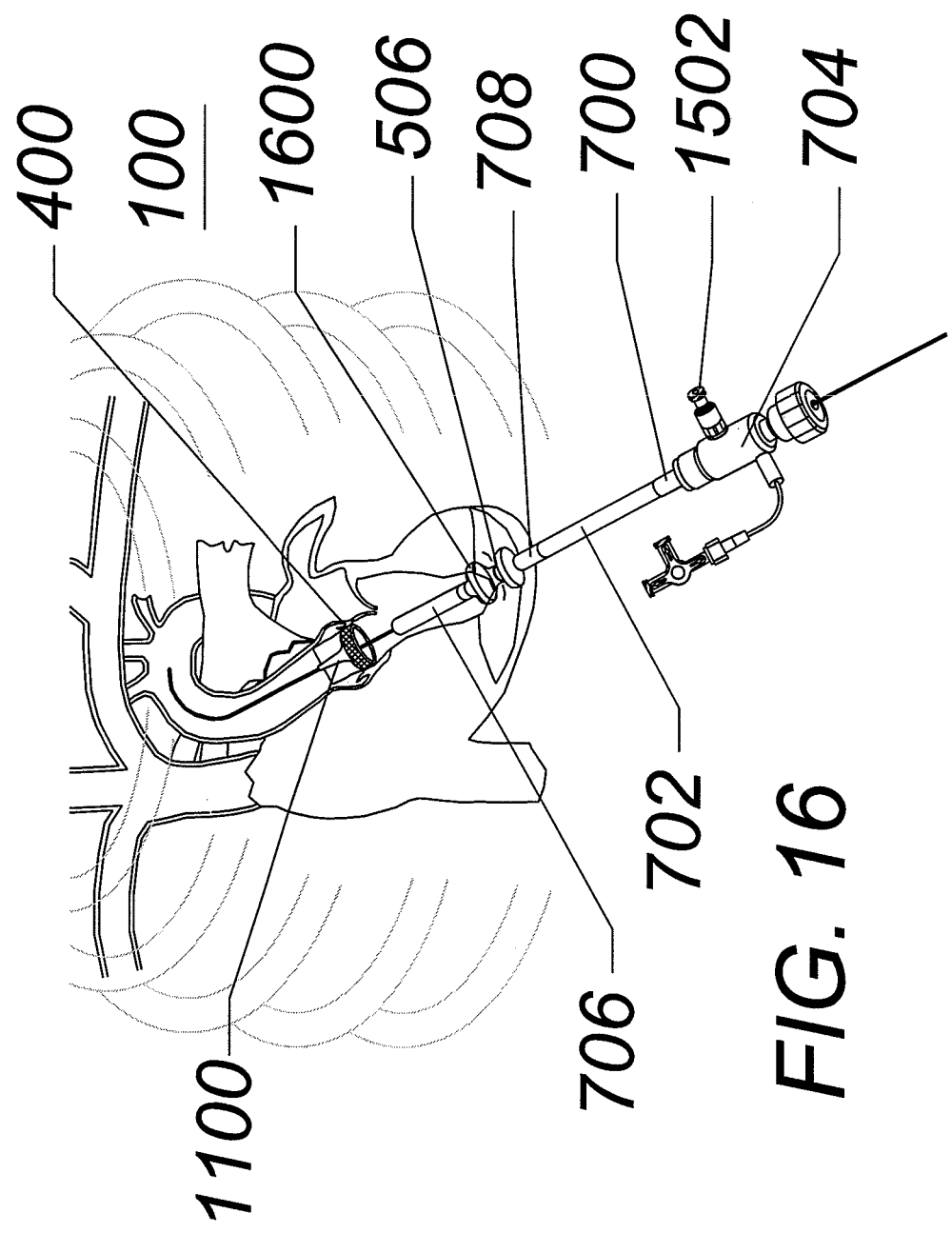
FIG. 16 illustrates a stabilization balloon affixed to the expandable transapical sheath, wherein the stabilization balloon is inflated across the ventricular entrance site, according to an embodiment of the invention.

FIG. 16 illustrates yet another embodiment of the expandable transapical sheath 700 further comprising a sealing balloon system 1600. The expandable valve 1100 is firmly implanted within the annulus of the diseased aortic valve 400. The sealing balloon 1600 is affixed to the outside of the expandable distal region 706. The sealing balloon 1600 can also be affixed to the non-expandable proximal region 702. The sheath hub 704 further comprises the balloon inflation port 1502, operably connected to the interior of the sealing balloon 1600 by way of inflation lumens within the wall of the sheath tubing 702, 706, and 708. The sealing balloon 1600 is advantageously fabricated from elastomeric materials and is a generally low-pressure balloon. The sealing balloon 1600 can be fabricated from polyurethane, silicone elastomer, thermoplastic elastomer, or the like. The relaxed wall thickness of the sealing balloon 1600 can range between 0.005 to 0.010 inches and preferably between 0.001 and 0.005 inches. The rated inflation pressure of the sealing balloon 1600 is generally two atmospheres or less. The sealing balloon 1600 is long enough to span the myocardium at the ventricular apex and expand both inside the left ventricle and outside the heart to form a generally dumbbell shape when inflated. The sealing balloon 1600 serves to stabilize the sheath 700 within the heart, minimizing the chance of inadvertently dislodging the sheath retrograde or antegrade. When removal is desired, the sealing balloon 1600 can be deflated to remove the sheath 700 from the heart. In other embodiments, the sheath distal region 706 can be reduced in diameter while retaining the sheath 700 in place in through the puncture site 506. The sealing balloon 1600 can be used to maintain a light seal against blood loss through the puncture site 506 as the puncture site 506 relaxes closed around the diametrically shrinking sheath tubing.

Figure 17:
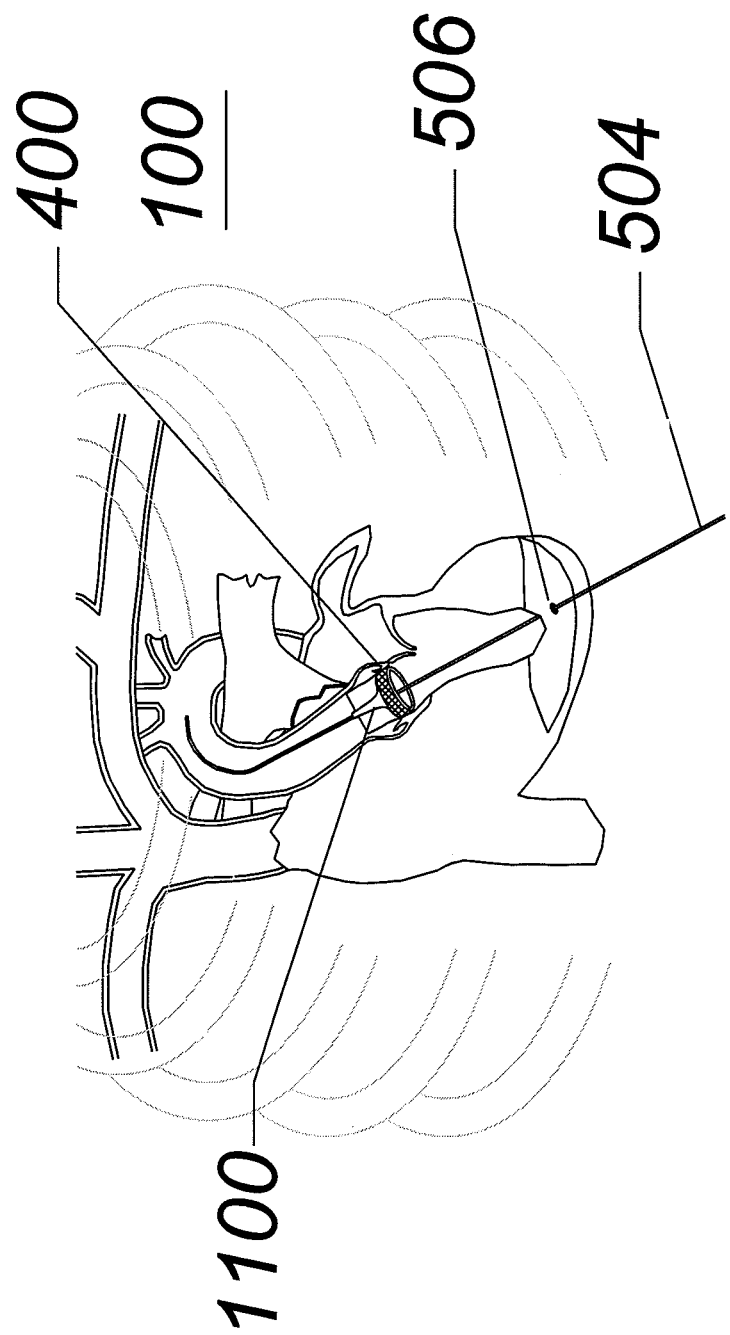
FIG. 17 illustrates the implanted aortic valve prosthesis in place within the aortic outflow tract with the expandable transapical sheath having been removed and a guidewire still in place, according to an embodiment of the invention.

FIG. 17 illustrates the patient 100 with the replacement aortic valve prosthesis 1100 in place within the natural aortic valve 400 annulus. The guidewire 504 remains in place through the prosthesis 1100 and through the puncture site 506, which was stretched but not torn by the procedure and relaxes back to its closed position. A major benefit of using the expandable transapical sheath 700, as described in FIGS. 7 through 16, is its ability to radially dilate tissue, rather than tearing tissue. Instead of a cutdown on the ventricular myocardium, a needle puncture, followed by radial dilation can be performed to achieve a minimally invasive access without undue tissue trauma. The transapical sheath 700 can reduce tissue trauma, improve healing, maintain a higher level of ventricular function, and improve patient outcomes relative to transapical procedures where an incision is made in the ventricular myocardium followed by tearing of the tissue to insert a non-expandable sheath.

Figure 18:
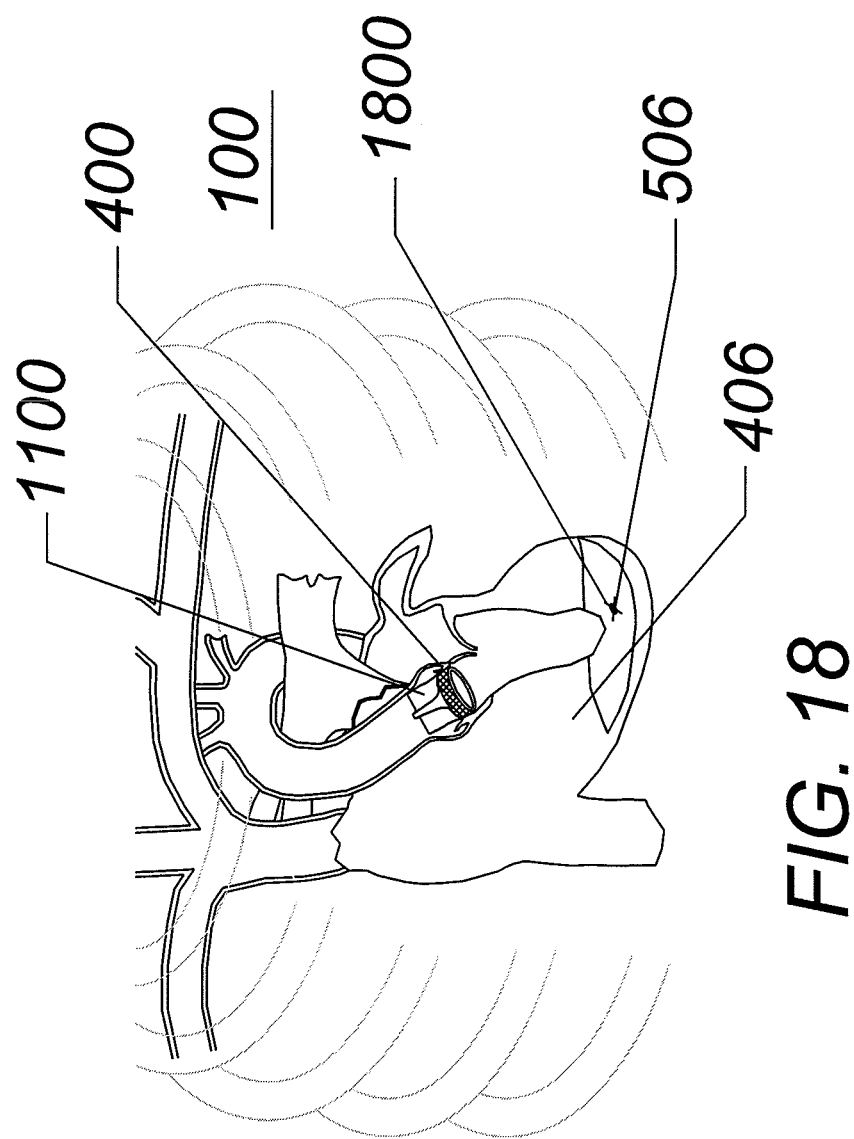
FIG. 18 illustrates the implanted aortic valve prosthesis in place within the aortic outflow tract and the entrance site closed with sutures or other closure device, according to an embodiment of the invention.

FIG. 18 illustrates the patient 100 with the replacement aortic valve prosthesis 1100 firmly seated in place within the annulus of the natural aortic valve. A plurality of stitches 1800 are used to perform final closure of the myocardial puncture site 506. Other types of commercial medical closure devices may also be applicable for this procedure. The pericardium 406 is yet to be closed but closure is advantageously performed using sutures to close the natural pericardium. Optionally, pericardial patches fabricated from glutaraldehyde cross-linked bovine or porcine pericardium can be sutured in place to close a large gap in the human pericardium. The stitches 1800, in the illustrated embodiment comprise two sutures placed across the puncture site 506 in a cross or "X" pattern. Other combinations or patterns can also be used. The thoracic access site can now be closed using standard sutures or other accepted open surgical closure methodology.

FIG. 19A illustrates a side view of an embodiment of the expandable transapical sheath 700 such as the sheath 700 described above. In the illustrated embodiment, the sheath 700 comprises the proximal non-expandable tubing 702, the sheath hub 704, the distal expandable tubing 706, the transition zone 708, and the dilator 710. The expandable distal region 706 and part of the transition zone 708 of the sheath 700 further comprise one or more longitudinal folds 1904. The sheath 700 comprises the tapered nose fairing 712, a dilator balloon 1906, a sheath hemostasis valve 1910, a guidewire 504, a dilator hub 806, a dilator inflation port 804, a dilator hemostasis valve 1902, a dilator purge port 1914, a length of dilator outer tubing 1920, a sheath radiopaque marker 1936, and a sheath purge port 1912.

Referring to FIG. 19A, the sheath hub 704 can be coupled to the proximal end of the non-expandable tubing region 702. The distal end of the non-expandable tubing region 702 can be coupled to the proximal end of the distal expandable region 706 by the transition zone 708. The dilator 710 can be slidably disposed within the lumen of the sheath 700 and held in place axially by compression of a lock or sheath valve 1910 on the hub 806 or tubing of the dilator 710. The dilator 710 can be further held in place by collapse and radial compression of the expandable distal region 706. The dilator balloon 1906 can be bonded, welded, or otherwise affixed to the dilator catheter tubing 1908 by balloon bonds 1932 at both ends of the dilator balloon 1906. The dilator balloon 1906 can be fully deflated and wrapped around the dilator catheter tubing 1908 prior to insertion inside the sheath. The dilator hub 806 can be coupled to the proximal end of the dilator catheter tubing 1908. The dilator inflation port 804 can be coupled to the dilator hub 806 and can be operably connected to a balloon inflation lumen within the hub 806 and within the dilator tubing 1920 or 1908, or an annulus 1922 (not shown) between the two dilator tubes 1908 and 1920. The sheath radiopaque marker 1936 can be coupled to, or embedded within, the folded distal section 706.

The sheath purge port 1912 can be coupled to the sheath hub 704 and can comprise a flexible length of axially elongate tubing with a central lumen. The sheath purge port 1912 is preferably terminated with a Luer lock fitting or a stopcock or other type of valve. The sheath purge port 1912 can be operably connected to the interior lumen of the sheath and is suitable for purging of air or aspiration of fluids therethrough. The dilator purge port 1914 can be coupled to the dilator hub 806 and is operably connected to the central guidewire lumen of the dilator 710. The dilator purge port 1914 is preferably terminated with a Luer lock fitting or a stopcock or other type of valve. The dilator purge port 1914 can be operably connected to the interior lumen of the sheath and is suitable for purging of air or aspiration of fluids therethrough.

The sheath hub 704 preferably comprises ports that further comprise, or are terminated by, hemostasis valves 1910. The hemostasis valves 1910 are configured to prevent hemorrhage from, or air intake into, the lumen of the sheath subassembly 1900. The hemostasis valves 1910 can comprise between one and 5 elements to form a seal against nothing inserted into the valve, form a seal against a maximum diameter object inserted through the valve, and form a seal against anything of intermediate size inserted through the valve. The hemostasis valve elements 1910 can be fabricated from soft silicone or other elastomer. The hemostasis valve elements 1910 can be coated or impregnated with lubricious coatings such as silicone oil or hydrophilic layer. The hemostasis valve elements can comprise duckbill valves, pinhole valves, slit valves, X-slit valves, ring seals, and the like. The sheath hub 704, and any other housings associated therewith, can be fabricated from relatively rigid polymers such as, but not limited to, acrylonitrile butadiene styrene (ABS), polyurethane, PVC, PET, polycarbonate, polysulfone, and the like.

In FIG. 19A, the distal expandable region 706 and the transition zone 708 are illustrated in their first, smaller cross-sectional configuration. The transition zone 708 forms a taper between the diametrically collapsed expandable region 706 and the larger proximal non-expandable tube or region 702. The sheath radiopaque marker 1936, which can number between 1 and 5, is shown located near the distal end of the expandable, distal region 706. The sheath radiopaque marker 1936 can be fabricated from gold, platinum, or tantalum wire and can be wound and embedded within the wall of the distal region 706. Radiopaque wire diameters ranging from 0.001 to 0.005 inches in diameter can be used for this application and approximately 3 to 10 winds, with a preferred number of 4 to 6 winds offer suitable visibility under fluoroscopy. The wires have the benefit of being able to be folded or creased along with the rest of the distal expandable region.

The distal sheath tubing 706 is folded longitudinally in a predetermined pattern comprising between one and four exterior fold edges, wherein the folds extend all the way from the proximal end of the transition zone 708 to the distal end of the distal sheath tube 706. In the illustrated embodiment, the distal portion 706 comprises a longitudinal fold 1904 running parallel to the longitudinal axis of the distal portion 706. The fold 1904 comprises two outer edges and an internal edge with the outer edges disposed one on each side of the internal edge. The fold 1904 extends from the distal end of the distal portion 706 to the proximal end of the distal portion 706 and extends across a substantial portion of the transition zone 708 to a point where it dissipates near the proximal end of the transition zone 708. Further details of the longitudinal fold 1904 will be described below.

The distal end of the distal portion 706 can be covered with the proximal end of the distal fairing 712. The distal fairing 712 can be configured to cover the distal exposed edge of the distal sheath tube 706 to provide a smooth taper against which the sheath system 700 can be advanced into the myocardium. The distal fairing 712 can be elastomeric and can be stretched slightly over the distal end of the distal portion 706. The distal fairing 712 can be coupled to the inner dilator tube 1908 by bonding, welding, or the like. The distal fairing 712 can be fabricated from elastomeric materials such as, but not limited to, Hytrel, Pebax, silicone, thermoplastic elastomer, polyurethane, or the like. The distal fairing 712 can further comprise with barium sulfate or bismuth sulfate in concentrations between 5% and 40% to improve radiopacity. The guidewire 504 is a separate device over which the sheath 700 rides, but is illustrated inserted through the central lumen of the dilator 710.

FIG. 19B illustrates the transapical sheath subassembly 1900 following expansion of the balloon 1906 on the dilator 710, re-collapse of the dilator balloon 1906, and subsequent removal of the entire dilator 710. The sheath subassembly 1900 is illustrated in partial breakaway view. The sheath subassembly 1900 is illustrated in its second, fully expanded, larger configuration. Expansion has occurred in the distal expandable region 706 and in the transition zone 708. Expansion, as defined herein, describes dimension changes in a direction lateral to the longitudinal axis of the sheath subassembly 1900. The sheath subassembly 1900 comprises the distal portion 706, the transition zone 708, the proximal portion 702, the sheath hub 704, the hemostasis valve 1910, and the sheath purge port 1912. The proximal portion 702 further comprises a braid reinforcement 1924 and an optional coil reinforcement 1928. The distal portion 706 further comprises a malleable coil reinforcement 1930, one or more radiopaque markers 1936, an optional stabilization and sealing balloon 1600, an inner polymer layer 1942, an outer polymer layer 1940, and an optional braid reinforcement 1926. The transition zone 708 can comprise reinforcement elements from the proximal region 702, the distal region 706, or both. The transition zone 708 can blend the properties of the proximal region 702 and the distal region 706. The properties of the two regions 702 and 706 can be interdigitated within the transition zone 708 such that tapered fingers describe the boundary therebetween. The hub 704 further comprises the optional stabilization balloon inflation port 1502 and the optional electrical input connector for resistive heating of shape memory reinforcing structures 1926, 1930, or both.

Malleable reinforcing structures within the transition zone 708 and the distal expandable region maintain the sheath in its second, larger, cross-sectional configuration. The reinforcing elements can comprise structures such as, but not limited to, spiral windings of flat or round wire, braided elements of polymeric strands, wire, a mesh structure similar to a stent, a slotted tube with overlapping longitudinally oriented slots, or the like. In an alternative embodiment, the distal expandable region 706 can comprise reinforcing elements 1930, 1926 similar to those used in the proximal expandable region 702. The polymers used in the distal expandable region can include materials such as, but not limited to, polyethylene, HDPE, LDPE, polyethylene blends, Hytrel, Pebax, and the like. Malleable materials such as the polyethylene materials plastically deform under force of the dilator balloon and offer the benefit of remodeling from a small diameter flexible structure to a large diameter, relatively inflexible structure capable of guiding catheters therethrough. In yet other embodiments, the distal expandable region 706 can comprise shape-memory reinforcing elements that can be heated or cooled to generate austenite or martensite conditions, respectively, that further can be used to drive the sheath wall from one cross-sectional configuration to another. The radiopaque marker 1936 is now malleably expanded to conform to the sheath cross-sectional shape in the distal expandable region 706.

In practice, an inner sheath layer 1942 is first laid down over a PTFE-coated stainless steel mandrel (not shown). The sheath inner layer 1942 is preferably fabricated from lubricious materials such as, but not limited to, polyethylene, HDPE, LDPE, blends of HDPE and LDPE, PTFE, FEP, PFA, Hytrel, Pebax, or the like. The sheath inner layer 1942 can also be coated, on its inner surface, with friction retarding materials such as, but not limited to, silicone oil, polyurethane-based hydrophilic slip coating materials, and the like. The mesh layers 1924 and 1926 are next applied over the inner layer 1942. The coil reinforcement layers 1928 and 1930 are next applied over the mesh reinforcement layers 1924, 1926. In other embodiments, a second layer of mesh can optionally be applied over the coil layers 1928, 1930. The second layer of mesh can have different properties from the inner layer, including different filament diameter, filament count, number of picks, and filament density or angle. Finally, an outer layer of polymeric material 1940 is applied over the reinforcement, after which shrink tubing is placed around the entire structure and heated to shrink, melt, fuse, and bond the inner layer 1942 to the outer layer 1940 while sandwiching the reinforcing layers therebetween. The outer layer 1940 melts and bonds to the inner layer 1942 through the spaces between the coil layers 1928, 1930 and the mesh layers 1924, 1926. The sheath inner layer 634 can have a wall thickness ranging between about 0.001 and 0.010 inches with a preferred range of about 0.002 and 0.006 inches. The sheath outer layer 632 can have a wall thickness ranging between about 0.001 and 0.010 inches with a preferred range of about 0.001 to 0.006 inches.

The mesh 1924, 1926 can be formed from a braid, weave, knit or other structure formed into a tubular cross-section. The mesh 1924, 1936 can be fabricated from flat or round strands. The mesh 1924, 1936 can be fabricated from polymers such as, but not limited to, polyethylene naphthalate (PEN), PET, polyamide, polyimide, or the like. The mesh 1924, 1936 can also be fabricated from metals such as, but not limited to, malleable stainless steel, spring stainless steel, nitinol, titanium, cobalt nickel alloy, tantalum, gold, platinum, platinum alloy, and the like. The lateral size of the strands of the mesh 1924, 1936 can range between 0.001 and 0.010 inches in at least one dimension. The number of ends of the mesh 1924, 1936 can range between 2 and 50. The mesh 1924, 1936 can comprise a pick count of between about 10 and 100 per inch with a preferred range of about 20 to 80 picks per inch.

The construction of the distal sheath tube 706 can comprise a coil of wire 1930 with a wire diameter of 0.001 to 0.040 inches in diameter and preferably between 0.002 and 0.010 inches in diameter. The coil 1930 can also comprise a ribbon wire or a flat wire that is 0.001 to 0.010 inches in one dimension and 0.004 to 0.040 inches in the other dimension. Preferably, the flat wire is 0.001 to 0.005 inches in the small dimension, generally oriented in the radial direction of the coil, and 0.005 to 0.020 inches in width, oriented perpendicular to the radial direction of the coil. The pitch of the coil 1930, which is related to the spacing between coil turns can range from about 0 to about 5 times the ribbon width or wire diameter. Preferably, some space exists between the coil turns to permit bonding between the outer layer 1940 and the inner layer 1942 so a preferred spacing is between 0.5 and 4 times the width of the ribbon. The outer layer 1940 of polymeric material can have a wall thickness of 0.001 to 0.020 inches and the inner layer 1942 has a wall thickness of between 0.001 and 0.010 inches. The wire used to fabricate the coil 1930 can be fabricated from annealed materials such as, but not limited to, gold, stainless steel, titanium, tantalum, nickel-titanium alloy, cobalt nickel alloy, and the like. The wire is preferably fully annealed. The wires can also comprise polymers or non-metallic materials such as, but not limited to, PET, PEN, polyamide, polycarbonate, glass-filled polycarbonate, carbon fibers, or the like. The wires of the coil reinforcement 1930 can be advantageously coated with materials that have increased radiopacity to allow for improved visibility under fluoroscopy or X-ray visualization. The radiopaque coatings for the coil reinforcement may comprise gold, platinum, tantalum, platinum-iridium, and the like. The mechanical properties of the coil 1930 are such that it is able to control the configuration of the fused inner layer 1942 and the outer layer 1940. When the distal region 706 is folded to form a small diameter, the polymeric layers 1940, 1942, which can have some memory, do not generate significant or substantial springback. The sheath wall is preferably thin so that it any forces it imparts to the tubular structure are exceeded by those forces exerted by the malleable distal reinforcing layers 1930, 1942. Additionally, a peel away, slide away, or otherwise removable protective sleeve (not shown) is useful but not necessary to maintain the collapsed sheath configuration.

The entire sheath subassembly 1900, which comprises a central lumen (not shown), comprises an approximately constant inner diameter along its entire length. The approximately constant diameter is beneficial in that objects of large diameter, such as prosthetic heart valves, can be inserted and advanced completely from the proximal end and out the distal end of the sheath subassembly 1900. The sheath subassembly 1900 is illustrated in partial breakaway view to show the coil reinforcement layers 1928 and 1930 along with the mesh 1924 and 1936. The optional electrical input connector 1940 is affixed to, and operably connected to, an electrical bus 1942 (FIG. 20A) running within the wall of the proximal portion 702, the transition zone 708, and the distal region 706 as well as within the hub 704. The distal end of the electrical bus 1942 (FIG. 20A) is affixed to, and operably connected to, either one or both reinforcement layers 1930 or 1926. The sealing balloon input port 1502 is preferably terminated with a Luer lock female fitting and is operably connected to a balloon inflation lumen 1944 (FIG. 20B) within the wall of the proximal portion 702, the transition zone 708, and the distal portion 706, as well as within the hub 704. The balloon inflation lumen 1944 is small and can extend as a bump, in cross-section, that extends outside the normal outside diameter of the sheath walls.

FIG. 19C illustrates the dilator 710 following removal from the sheath subassembly 1900. The dilator balloon 1906 is illustrated in its expanded configuration for the purpose of clarity. The dilator 710 comprises the outer dilator shaft 1920 further comprising the outer dilator shaft lumen 1922, the inner dilator shaft 1908 further comprising a guidewire lumen 1934, the dilator balloon 1906 further comprising an internal volume 1916, the proximal and distal balloon bonds 1932, the dilator hub 806, the dilator inflation port 804, the dilator hemostasis valve 1902, and the dilator purge port 1914.

Referring to FIG. 19C, the dilator balloon 1906 can be an angioplasty-type balloon, fabricated from materials such as, but not limited to, PET, PETG, polyamide, polyamide, copolymers of the aforementioned, reinforced polymers, or the like, with wall thickness ranging between about 0.0005 to 0.006 inches with a preferred range of about 0.0008 to 0.003 inches, and is capable of containing an internal pressure of 10 to 30 atmospheres, or higher. The dilator balloon 1906 is generally filled with incompressible fluid such as, but not limited to, saline, radiographic contrast media, Ringer's lactate, or the like by the operator, through a balloon inflation port 804, integral, or affixed, to the dilator hub 806.

The dilator balloon 1906 comprises diametric neck down regions, or bonds 1932, at its proximal end distal ends. The dilator balloon 1906 is affixed to the outer dilator shaft 1920 or the dilator hub 806 at the proximal neck down region 1932. The dilator balloon 1906 can be affixed to the sheath inner tubing 1908 at the distal neck down region 1932 using adhesives, welding, or a combination thereof. The dilator balloon 1906 comprises a flat length at least as long as the combined length of the sheath expandable distal region 706 and the transition zone 708, and is preferably somewhat longer to facilitate manufacturability and reliability. The dilator balloon 1906 can comprise an inflated diameter approximately equal to or slightly greater than that of the fully expanded distal region 706 of the sheath. Note that the distal fairing 712, which is beneficially fabricated from soft elastomeric materials expands and folds distally off the shoulders of the balloon 1906 such that when the balloon 1906 is deflated, the fairing 712 returns to a small diameter that can be withdrawn proximally through the lumen of the sheath subassembly 1900.

In some embodiments, a long proximal neck down region is provided on the balloon 1906. In these embodiments, fluid pressure applied to the inflation port 804 on the dilator hub 806 is operably connected to the annulus between the dilator balloon 1906 and the inner catheter shaft 1908, allowing balloon inflation fluid such as radiopaque dye contrast media, saline, or the like to be routed into the balloon internal structure and causing the balloon to forcibly expand diametrically. This arrangement can result in a beneficial increase in rated balloon burst, or inflation, pressure. Rated balloon burst pressures in excess of about 25 to 30 atmospheres can be achieved with 99.9% reliability and 95% confidence. In yet other embodiments, the fluid pressure is applied to the balloon through the annulus 1922 within the dilator outer tubing 1920 not occupied by the inner tubing 1908.

In other embodiments, the expandable region 706 can comprise shape memory reinforcing elements 1926 or 1930, or both, fabricated from nitinol, which is configured with an austenite finish temperature, and preferably the austenite start temperature, in excess of body temperature (normally around 37 degrees centigrade). In this embodiment, the sheath system 700 can be inserted into the heart. In its first, martensitic configuration, the reinforcing elements 1926, 1930 can be expanded malleably using the dilator 710 as shown in FIG. 19C. At the end of the procedure, the expandable region 706 can be heated by application of electricity to generate resistive heating, causing a temperature increase to above the austenite finish temperature. A suitable austenite finish temperature can range from 38 to 50 degrees centigrade. Such heating can be performed at the conclusion of the procedure, following removal of any therapeutic or diagnostic instruments from the center of the sheath. The shape memory elements can be heat set to a collapsed, small diameter configuration to which they will be biased following application of resistive heating. The reinforcing structures can be configured as a braid, a spiral winding, a woven mesh, a slotted tube, or the like. For the purpose of manufacturing, the reinforcing structures can be heat set in a collapsed, or small diameter, configuration and then be cooled to below martensite finish temperature, at which point the reinforcing structures can be expanded for coating with a polymer or other suitable manufacturing process.

In the re-collapsible embodiments, the expandable region 706 can be re-collapsed to its third, smaller cross-sectional configuration by application of heat to the shape-memory reinforcement embedded within the expandable region. The expandable region 706 can be made to uniformly compress to a smaller diameter, or it can be made to fold into any of a variety of cross-sectional patterns exhibited by a tube that is folded along longitudinally disposed folds. In the embodiments where uniform reduction in cross-sectional shape is imparted, the reinforcement can comprise a braid that elongates longitudinally when it reduces its diameter. The polymeric surround of the expandable region 706 is preferably elastomeric and comprises materials such as, but not limited to, polyurethane, thermoplastic elastomer, silicone elastomer, and the like. The interior of the wall of the expandable region is advantageously coated with a layer of high lubricity and low friction to facilitate catheter or device introduction therethrough without hang-up. Such low friction structures include fluoropolymers such as, but not limited to, PTFE, PFA, FEP, and the like. The interior can also be coated with silicone oil, hydrophilic layers such as those fabricated using polyurethane, and the like.

In another embodiment, the expandable region 706 can be maintained with an open inner lumen if a hollow sleeve or dilator (not shown) is inserted therethrough, or if the expandable region 706 has at least some hoop strength gained by appropriate wall design or reinforcement within the wall. The hollow sleeve or dilator (not shown) can comprise a hollow axially elongate tube with a proximal end and a distal end. The tube can comprise structures and materials that impart flexibility to the hollow sleeve or dilator but the tube advantageously comprises the properties of column strength and kink-resistance. The proximal end of the tube comprising the hollow sleeve or dilator can be affixed to a sleeve hub. The structure of the tube comprised by the hollow sleeve or dilator is preferably very thin and can further comprise a single material, preferably polymeric, or it can comprise a built-up, composite structure with a reinforcing layer and a polymeric surround. The reinforcing layer can comprise a braid, weave, helical coil, slotted tube, or the like. In a preferred embodiment, the hollow sleeve or dilator tube can comprise polymeric surround materials such as, but not limited to, polyamide, polyamide, polyurethane, polyester, polyether ether ketone, Hytrel, or the like. The length of the hollow sleeve or dilator tube is sufficient to extend from the proximal end of the sheath hub 704 to the distal end of the expandable region 706 while the hollow sleeve hub extends out the proximal end of the sheath 700. The distal end of the hollow sleeve or dilator tube can comprise a bevel on its outer surface to assist with coercing the sheath expandable region 706 to expand from its first, smaller cross-sectional area to its second, larger cross-sectional area. The distal end of the hollow sleeve or dilator tube can further comprise shape-memory elements that are bent radially inward at the distal end in their Martensitic phase and then, upon exposure to body temperature blood, they expand radially outward to form a straight, non-inwardly beveled distal end. In yet another embodiment, an obturator is provided which closely fits the inside diameter of the hollow sleeve or dilator tube and which comprises a tapered distal end suitable for advancement into a body lumen, vessel, or expandable sheath tube. The hollow sleeve or dilator tube is advanced into the expandable sheath as a unit. The obturator can comprise a hub at its proximal end that releasably snaps or connects to the distal end of the hollow sleeve or dilator tube hub. Once the composite structure is advanced completely into the expandable sheath, the obturator can be removed revealing the large central lumen suitable for the introduction of catheters, instruments, implants, and the like.

The dilator 710 is slidably disposed within the central lumen of the sheath subassembly 1900 and further comprises an expandable dilator such as, but not limited to, an angioplasty type balloon (as illustrated), a malecot, a reverse collet, or other device capable of expansion to approximately 0.2-mm (0.5 French), or greater, larger than the diameter of the sheath. The balloon 1906 can be inflated through the inflation lumen within the catheter shaft, which is operably connected, at its proximal end, to a dilator hub or inflation port. Following inflation, which expands the distal end 706 of the sheath 700, the dilator expansion element, such as the balloon 1906, can be deflated or collapsed, following which it can be removed from the sheath subassembly 1900 along with the distal fairing or nose cone 712.

In other embodiments, the exterior of the sheath, and optionally the internal lumen of the sheath, can be coated with a lubricious coating comprising materials such as, but not limited to, silicone oil or a hydrophilic hydrogel comprising polyethylene glycol, polyether polyurethane, or the like. Other coatings can include antimicrobial coatings such as those fabricated from silver azide or anticoagulant coatings such as those comprising heparin.

The prosthetic valve delivery catheter 1000 is configured to deliver the collapsed prosthetic valve 1100 to an implantation site within the patient. Typical valves include aortic and mitral valve replacements. The prosthetic valve 1100 further comprises an expandable stent support, valving elements, and fixation elements. The valving elements are suspended within, or around, the expandable stent and can comprise between one and four leaflets fabricated from polyurethane, cross-linked pericardium, fixed natural porcine aortic roots, or homografts. The outside diameter of the collapsed prosthetic valve 1100 is such that the valve 1100 can be slidably advanced through the lumen of the sheath subassembly 1900, following removal of the dilator 710. In some embodiments, the valve delivery catheter 1000 can comprise an external sleeve 1002 to retain the valve 1100 in its smallest possible diameter during placement into the patient. The expandable stent support can be malleable and balloon expandable, self-expanding, or self expanding with balloon expansion augmentation.

Any additional components, including inflation devices, the guidewire 504, stopcocks, secondary sheaths, as well as the expandable transapical sheath system 700 can be provided in a kit, or packaged together for the convenience of the user. All components can be sterilized using ethylene oxide, electron beam sterilization, or radiation sterilization, the latter at dosages of, for example, about 25 to 40 kGray. The components of the kit can be packaged in a single aseptic or double aseptic packaging system.

Figure 20A:
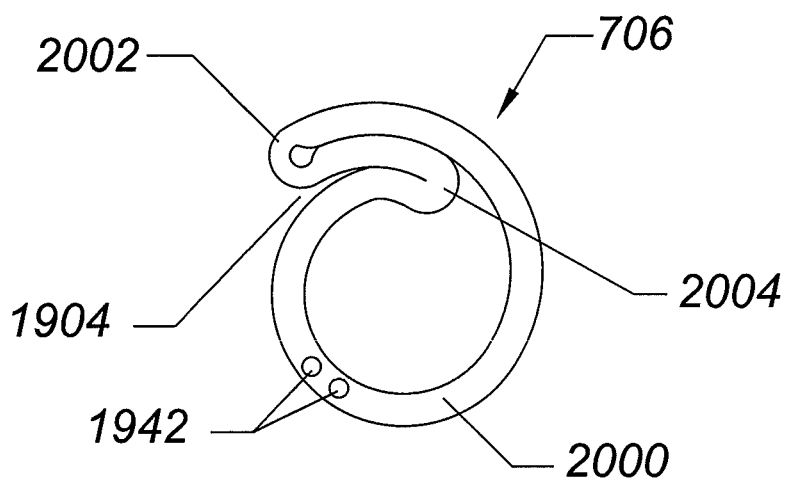
FIG. 20A illustrates a lateral cross-sectional view of the distal expandable portion of the expandable transapical sheath subassembly wherein the fold comprises a single outside edge and a single inside edge, according to an embodiment of the invention.

FIG. 20A illustrates a lateral cross-sectional view of a folded distal section 706 comprising a distal section wall 2000. The distal section wall 2000 comprises a single fold 1904 further comprising a single outside edge 2002 and a single inside edge 2004. With a small diameter distal section 706 and a relatively thick wall 2000, a single fold is the easiest structure to create during manufacturing. The sheath wall 2000 further comprises an optional electrical bus 1942 fabricated from stainless steel, silver, copper, or other conductor metal for use in transmitting electrical energy from the sheath hub to distal regions of the sheath.

Figure 20B:
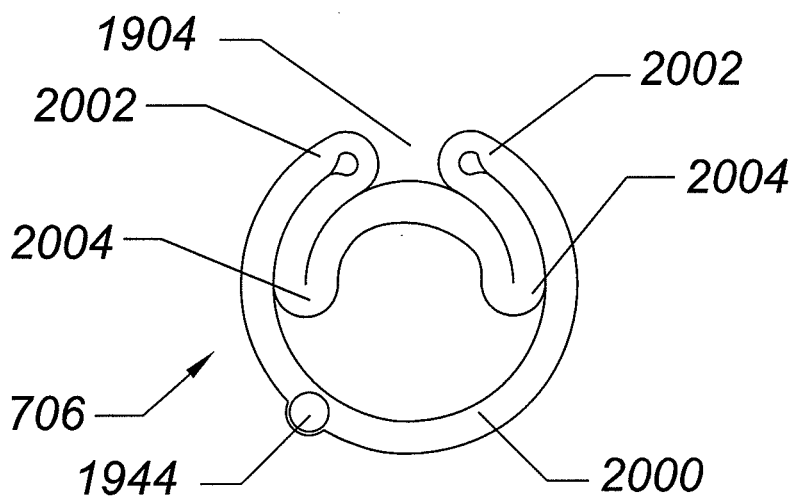
FIG. 20B illustrates a lateral cross-sectional view of the distal expandable portion of the expandable transapical sheath subassembly wherein the fold comprises two outside edges and two inside edges.

FIG. 20B illustrates a lateral cross-sectional view of a folded distal section 706 comprising a distal section wall 2000. The distal section wall 2000 comprises a double fold 1904 further comprising two outside edges 2002 and two inside edges 2004. When the diameter of the sheath increases, it becomes advantageous to form a plurality of folds in the wall 2000. For a sheath having a fully expanded outside diameter ranging between 12 French and 30 French and with a wall thickness ranging between 1 and 2-French, a double fold, as illustrated in FIG. 20B is preferred. A double fold, for example can allow a 14 French outside diameter sheath to fold into a collapsed diameter of around 9 to 12 French. An 18-French outside diameter sheath having a 1 to 2-French wall thickness can be folded into a collapsed diameter of around 12 to 13 French using a double fold. The sheath wall 2000 further comprises an optional balloon inflation lumen 1944 for use in transmitting fluidic pressure or energy from the sheath hub to distal regions of the sheath wherein a balloon may be affixed. The diameter of the balloon inflation lumen 1944 can range between 0.005 to 0.025 inches.

It should be appreciated in the embodiments described above that the longitudinal folds of FIGS. 20A and 20B or modifications thereof can be used to provide an expandable region of the catheter (described above) with an initial small cross-sectional diameter. By unfolding the distal region, the diameter of the distal region can be increased to a larger diameter. In the smaller folded configuration, the malleable structures described above can maintain the distal region in the smaller folded configuration. In other embodiments, an external structure can maintain the sheath in the folded configuration. In this smaller folder configuration it has been noted that the flexibility of the catheter (e.g., the ability of the catheter to navigate the aortic arch) is increased. When the catheter is unfolded and expanded, the malleable structure can reform to the larger unfolded diameter and to the shape of the anatomy in which the sheath his placed. In the unfolded configuration, the malleable structures provide hoop strength maintain the patency of the lumen.

It also should be noted that certain objects and advantages of the invention have been described above for the purpose of describing the invention and the advantages achieved over the prior art. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Moreover, although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. For example, it is contemplated that various combination or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow

We claim:

1. A method of introducing catheters into a ventricle of a heart, the method comprising the steps of:
    inserting a guidewire into the heart through a puncture in the myocardium in an apical region of a ventricle and routing the guidewire to a target region of the cardiovascular system;
    inserting a collapsed sheath with a dilator pre-inserted, over the guidewire and into the vasculature,
    radially expanding an expandable region of the sheath by pressurization of a balloon so that the expandable region radially dilates the myocardium and forms a lining inside the myocardium in the apical region of the ventricle;
    performing therapy or diagnosis at the target region through the expanded sheath;
    applying heat to cause a re-collapse of the expandable region of the sheath to a smaller diameter after performing therapy or diagnosis and prior to removing the sheath from the heart; and
    removing the sheath from the heart.

2. The method of claim 1 further comprising maintaining hemostasis at a proximal end of the sheath while performing therapy or diagnosis at the target region through the expanded sheath.

3. The method of claim 1 further comprising inserting therapeutic or diagnostic catheters through the expanded sheath.

4. The method of claim 3, further comprising removing the therapeutic or diagnostic catheters through the expanded sheath while maintaining hemostasis.

5. The method of claim 1, wherein the therapy comprises introducing a prosthetic valve delivery catheter through the expandable sheath.

6. The method of claim 1, wherein the therapy comprises delivering a valve prosthesis to the heart.

7. The method of claim 6, wherein the step of delivering a valve prosthesis further comprises the step of expanding a balloon within the valve prosthesis to expand a valve fixation stent to secure the valve prosthesis within the natural valve annulus.

8. The method of claim 6, wherein the step of delivering the valve prosthesis further comprises the step of releasing a self-expanding element comprised by the valve prosthesis and allowing the valve prosthesis and self-expanding element to expand and seat within the natural valve annulus.

9. The method of claim 1, wherein the therapy comprises the steps of introducing a second diametrically expandable delivery system through the sheath, expanding the second diametrically expandable delivery system, and delivering a valve prosthesis to a region of the heart through the expanded delivery system.

10. The method of claim 1, wherein the therapy or diagnostic procedure comprises introduction of a second diametrically expandable catheter through the expandable sheath.

11. A method of introducing catheters into a ventricle of a heart, the method comprising the steps of:
    inserting a guidewire into the heart through a puncture in the myocardium in an apical region of a ventricle and routing the guidewire to a target region of the cardiovascular system;
    inserting a collapsed sheath with a dilator pre-inserted, over the guidewire and into the vasculature, such that a proximal end of said collapsed sheath extends out of said puncture,
    radially expanding an expandable region of the sheath so that the expandable region radially dilates the myocardium and forms a lining inside the myocardium in the apical region of the ventricle;
    performing therapy or diagnosis at the target region through the expanded sheath;
    compressing the expandable region of the sheath to a smaller diameter after performing therapy or diagnosis and prior to removing the sheath from the heart; wherein compressing the expandable region of the sheath comprises reducing substantially uniformly a cross-sectional shape of the expandable region; and
    removing the sheath from the heart;
    wherein compressing the expandable region of the sheath comprises applying heat to the expandable region.

12. The method of claim 11, wherein reducing substantially uniformly the cross-sectional shape comprises longitudinally elongating the expandable region.

* * * * *